US012178520B2

(12) United States Patent
Ben-Yishai et al.

(10) Patent No.: US 12,178,520 B2
(45) Date of Patent: *Dec. 31, 2024

(54) MODEL REGISTRATION SYSTEM AND METHOD

(71) Applicant: ELBIT SYSTEMS LTD., Haifa (IL)

(72) Inventors: Rani Ben-Yishai, Haifa (IL); Lior Barak, Haifa (IL)

(73) Assignee: ELBIT SYSTEMS LTD., Haifa (IL)

(*) Notice: Subject to any disclaimer, the term of this patent is extended or adjusted under 35 U.S.C. 154(b) by 960 days.

This patent is subject to a terminal disclaimer.

(21) Appl. No.: 17/249,408

(22) Filed: Mar. 1, 2021

(65) Prior Publication Data

US 2021/0186355 A1 Jun. 24, 2021

Related U.S. Application Data

(63) Continuation-in-part of application No. 16/036,629, filed on Jul. 16, 2018, now Pat. No. 10,932,689, (Continued)

(30) Foreign Application Priority Data

Nov. 30, 2014 (IL) .......................... 236003

(51) Int. Cl.
*A61B 34/20* (2016.01)
*A61B 34/10* (2016.01)

(52) U.S. Cl.
CPC ............. *A61B 34/20* (2016.02); *A61B 34/10* (2016.02); *A61B 2034/107* (2016.02); *A61B 2034/2051* (2016.02); *A61B 2034/2055* (2016.02)

(58) Field of Classification Search
CPC ... A61B 34/20; A61B 34/10; A61B 2034/107; A61B 2034/2051; A61B 2034/2055; (Continued)

(56) References Cited

U.S. PATENT DOCUMENTS 5,588,430 A 12/1996 Bova et al.
6,122,541 A 9/2000 Cosman et al.
(Continued)

FOREIGN PATENT DOCUMENTS

CN 1668254 A 9/2005
CN 101170961 A 4/2008
(Continued)

OTHER PUBLICATIONS

International Search Report and Written Opinion issued on Mar. 27, 2016 for International Application No. PCT/IL2015/051160, 9 pages.
(Continued)

*Primary Examiner* — Joel Lamprecht
(74) *Attorney, Agent, or Firm* — KNOBBE, MARTENS, OLSON & BEAR, LLP

(57) ABSTRACT

A system for registering a coordinate system associated with a model of an object with a reference-coordinate-system, the object includes at least one marker, the system includes a portable-unit, a tracking-system and a processor. The portable unit includes and display and an optical-detection-assembly for acquiring at least one representation of the marker. The tracking-system tracks the position-and-orientation of the portable-unit in the reference-coordinate-system. The processor is configured to determine position-related-information respective of the marker in the reference-coordinate-system, to register the model with the reference-coordinate-system at least based on the position-related-information respective of the marker, and on a location of the marker in a coordinate system associated with the model, and to display registration-related-information on the display, at least one of the registration-related-information and the display location of the registration-related-informa-
(Continued)

tion is related to the position-and-orientation of the portable-unit in the reference-coordinate-system.

25 Claims, 31 Drawing Sheets

Related U.S. Application Data which is a continuation of application No. 15/531,685, filed as application No. PCT/IL2015/051160 on Nov. 29, 2015, now Pat. No. 10,022,065.

(58) Field of Classification Search
CPC .. A61B 2017/00951; A61B 2034/2065; A61B 2034/207; A61B 2090/3945; A61B 2090/502; A61B 5/055
See application file for complete search history.

(56) References Cited

U.S. PATENT DOCUMENTS

| | | |
|---|---|---|
| 6,235,038 B1 | 5/2001 | Hunter et al. |
| 6,259,943 B1 | 7/2001 | Cosman et al. |
| 6,529,765 B1 | 3/2003 | Franck |
| 6,640,127 B1 | 10/2003 | Kosaka et al. |
| 7,313,430 B2 | 12/2007 | Urquhart et al. |
| 7,556,428 B2 | 7/2009 | Sukovic et al. |
| 7,671,887 B2 | 3/2010 | Pescatore et al. |
| 7,747,312 B2 | 6/2010 | Barrick et al. |
| 7,920,909 B2 | 4/2011 | Lyon et al. |
| 8,010,177 B2 | 8/2011 | Csavoy et al. |
| 8,238,631 B2 | 8/2012 | Hartmann et al. |
| 8,380,288 B2 | 2/2013 | Labadie et al. |
| 8,392,022 B2 | 3/2013 | Ortmaier et al. |
| 8,483,434 B2 | 7/2013 | Buehner et al. |
| 8,657,809 B2 | 2/2014 | Schoepp |
| 10,022,065 B2 * | 7/2018 | Ben-Yishai ............ A61B 34/20 |
| 10,932,689 B2 * | 3/2021 | Ben-Yishai ............ A61B 5/055 |
| 2003/0055410 A1 | 3/2003 | Evans |
| 2003/0210812 A1 | 11/2003 | Khamene et al. |
| 2005/0015005 A1 | 1/2005 | Kockro |
| 2008/0119712 A1 | 5/2008 | Lloyd et al. |
| 2008/0306378 A1 | 12/2008 | Trousset et al. |
| 2008/0319491 A1 | 12/2008 | Schoenefeld et al. |
| 2010/0039506 A1 | 2/2010 | Sarvestani et al. |
| 2011/0009855 A1 | 4/2011 | Steven et al. |
| 2011/0085720 A1 | 4/2011 | Averbuch |
| 2011/0098553 A1 | 4/2011 | Robbins et al. |
| 2012/0004541 A1 | 1/2012 | Yamamoto et al. |
| 2012/0007823 A1 | 1/2012 | Ozawa et al. |
| 2013/0060146 A1 | 3/2013 | Yang et al. |
| 2013/0322719 A1 | 12/2013 | Dekel et al. |
| 2014/0005527 A1 | 1/2014 | Nagarkar et al. |
| 2014/0049629 A1 | 2/2014 | Siewerdsen |
| 2014/0107471 A1 | 4/2014 | Haider et al. |
| 2016/0015471 A1 | 1/2016 | Piron |

FOREIGN PATENT DOCUMENTS

| | | |
|---|---|---|
| CN | 103764061 A | 4/2014 |
| DE | 10161787 | 7/2003 |
| DE | 102005045706 | 4/2007 |
| DE | 102007013535 A1 | 9/2008 |
| EP | 1524626 | 4/2005 |
| EP | 1873666 A1 | 3/2009 |
| EP | 1800616 | 7/2011 |
| WO | 98/38908 A1 | 9/1998 |
| WO | 01/54558 A2 | 8/2001 |
| WO | 02/35454 A1 | 5/2002 |
| WO | 03/026505 A1 | 1/2005 |
| WO | 2006/027201 A1 | 3/2006 |
| WO | 2007/136745 A1 | 1/2008 |
| WO | 2008082574 A1 | 7/2008 |
| WO | 2008/130354 A1 | 10/2008 |
| WO | 2008/130355 A1 | 10/2008 |
| WO | 2008/130361 A1 | 10/2008 |
| WO | 2010/124672 A1 | 11/2010 |
| WO | 2011/134083 A1 | 11/2011 |
| WO | 2012/033552 A1 | 3/2012 |

OTHER PUBLICATIONS

"Marker Tracking and HMD Calibration for a Video-Based Augmented Reality Conferencing System", Hirokazu Kato and Mark Billinghurst, In Proceedings of the 2nd IEEE and ACM International Workshop on Augmented Reality (IWAR 99) 1999, IEEE Computer Society, Washington, DC, USA, pp. 85-94, Oct. 1999.

"Fast color fiducial detection and dynamic workspace extension in video see-through self-tracking augmented reality", Youngkwan Cho, Jun Park, and U. Neumann, In Proceedings of the 5th Pacific Conference on Computer Graphics and Applications (PG '97) 1997, IEEE Computer Society, Washington, DC, USA, pp. 168-177, Oct. 1997.

* cited by examiner

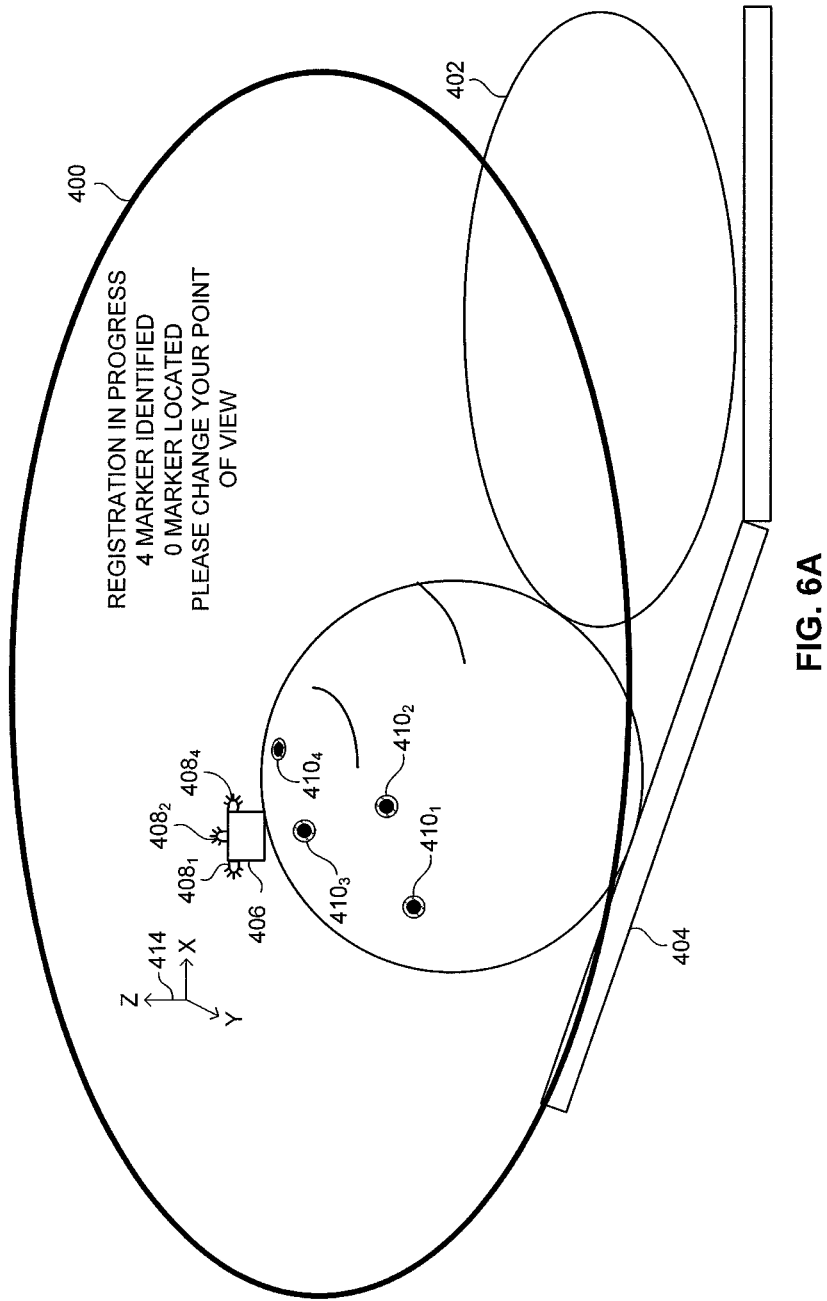

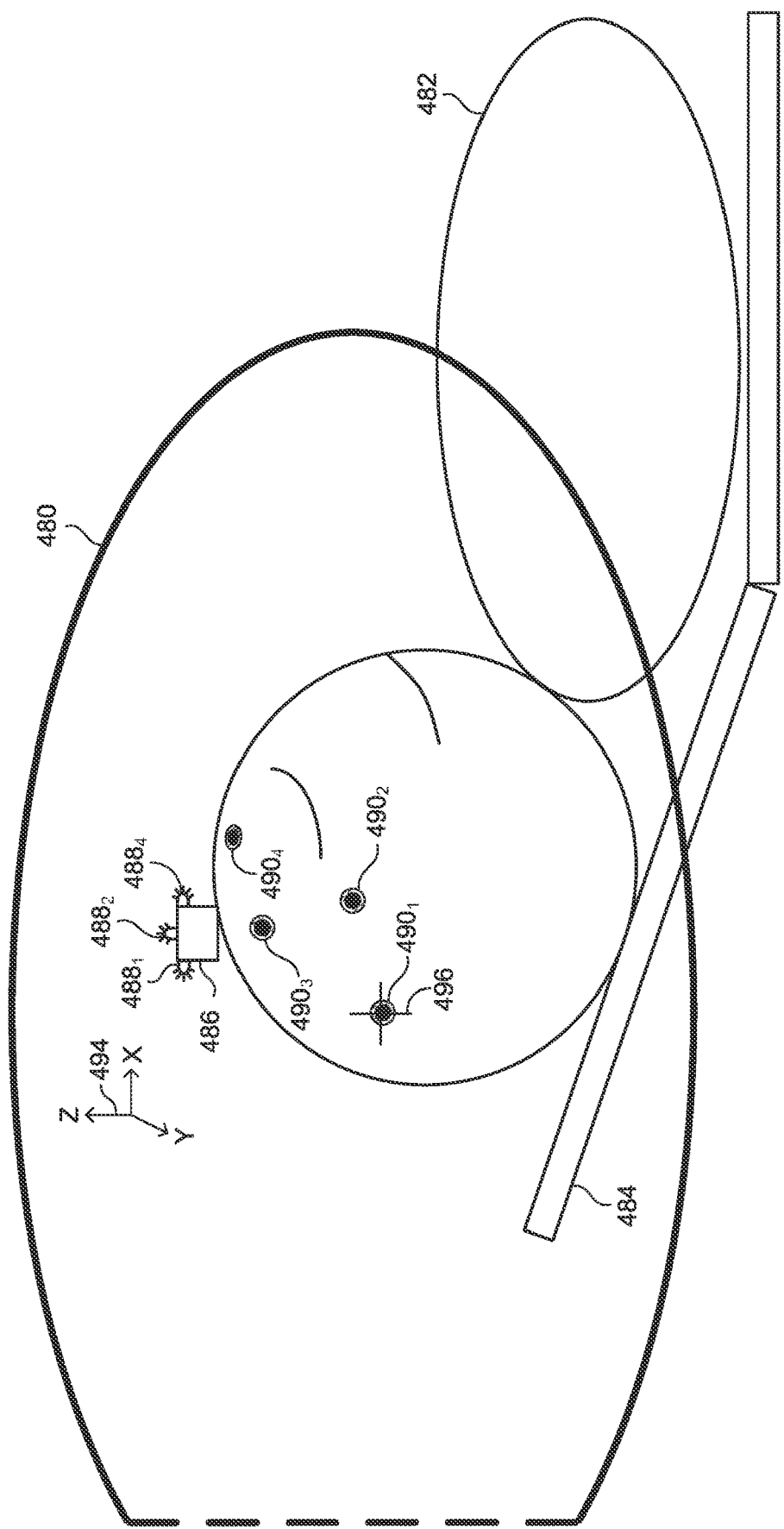

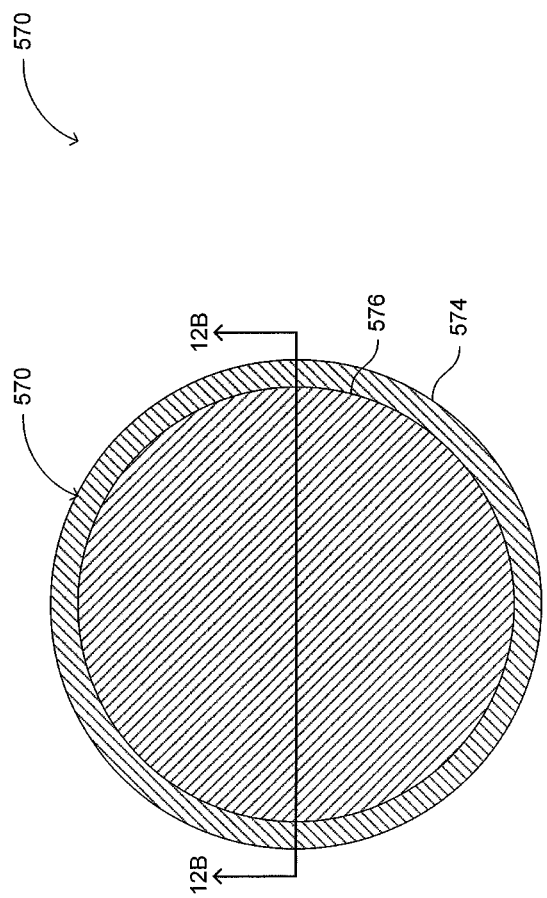
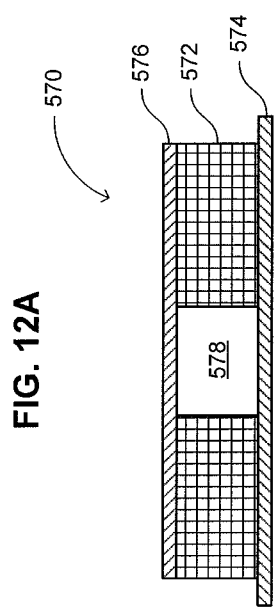
FIG. 12A
FIG. 12B

MODEL REGISTRATION SYSTEM AND METHOD

CROSS REFERENCE TO RELATED APPLICATIONS

This application is a continuation-in-part of U.S. patent application Ser. No. 16/036,629, filed on Jul. 16, 2018 and issued as U.S. Pat. No. 10,932,689 on Mar. 2, 2021, which is a continuation Application of U.S. patent application Ser. No. 15/531,685, filed on May 30, 2017 and issued as U.S. Pat. No. 10,022,065 on Jul. 17, 2018, which is the U.S. National Phase Application under 35 U.S.C. § 371 of International Application No. PCT/IL2015/051160, filed Nov. 29, 2015, which claims priority to Isreli Application No. 236003, filed on Nov. 30, 2014, the entire disclosure of each of which is hereby incorporated by reference.

TECHNICAL FIELD

The disclosed embodiments relate to tracking systems in general, and to system and methods for registering a model of an object with a reference coordinate system associated with a tracking system, in particular.

BACKGROUND

Registering the coordinate system associated with an image of the patient with the coordinate system associated with a medical tracking system enables the display of intraoperative information, (e.g., a representation of a medical tool, navigational information) on the image of a body part of interest of a patient, at the respective positions and orientations thereof. Thus, the user may see such intraoperative information along with the patient body part of interest.

U.S. Patent Application Publication U.S. 2011/0098553 to Robbins et al directs to an automatic registration of a Magnetic Resonance (MR) image with an image guidance system. The registration is achieved by placing MR visible markers at known positions relative to markers visible in a camera tracking system. The markers are fixed to a common fixture which is attached to a head clamp together with a reference marker (employed when the markers are covered or removed). The tracking system includes a camera with a detection array for detecting visible light and a processor arranged to analyze the output from the array. Each object to be detected carries a single marker with a pattern of contrasted areas of light and dark intersecting at a specific single feature point thereon with an array around the specific location. This enables the processor to detect an angle of rotation of the pattern and to distinguish each marker from the other markers.

U.S. Patent Application Publication 2012/0078236 to Schoepp, directs to a method for automatically registering the coordinate system associated with a navigation system with a coordinate system associated with a scan image. Initially, a camera assembly of a navigation system, which includes fiducial markers, is fixedly attached to the patient (e.g., with an adhesive). Thereafter, a scan image of the patient with the camera is acquired. Scan image includes the camera with the fiducial markers. The registration module automatically recognizes and identifies the fiducial markers visible in the scan image and determines the position of the camera assembly therefrom (i.e., the position of the fiducial markers with respect to the camera coordinate system and to the focal geometry of the camera are known). The registration module automatically registers the camera space with respect to the position of the patient in the scan image by identifying the position of the camera coordinate system within the scan image. Upon automatic registration of the camera, the tracking of a surgical tool is immediately available through the known relationships between the surgical tool, the camera coordinate system, the scan image coordinate system.

SUMMARY

An object of the disclosed embodiments is to provide a novel method and system for registering a model of an object with a reference coordinate system associated with a tracking system. In accordance with an aspect, there is thus provided a system for registering a coordinate system associated with a model of an object with a reference coordinate system. The object includes at least one marker. The system includes a portable unit, a tracking system and a processor. The processor is coupled with the portable unit and with the tracking system. The portable unit includes a display and an optical detection assembly for acquiring at least one representation of the at least one marker. The tracking system tracks the position and orientation of the portable unit in the reference coordinate system. The processor is configured to determine position related information respective of the at least one marker in the reference coordinate system, from the at least one representation and the position and orientation of the portable unit. The processor is further configured to register the model with the reference coordinate system at least based on the position related information respective of the at least one marker in the reference coordinate system, and based on a location of the at least one marker in the coordinate system associated with the model. The processor is further configured to display registration related information on the display. At least one of the registration related information and the display location of the registration related information is related to the position and orientation of the portable unit in the reference coordinate system.

In accordance with an aspect, there is thus provided a method for registering a coordinate system associated with a model of an object with a reference coordinate system. The object includes at least one marker. The method includes the procedure of acquiring at least one representation of the at least one marker and tracking the position and orientation of a portable unit in the reference coordinate system. The method further includes the procedures of determining position related information respective of the at least one marker in the reference coordinate system, from the at least one representation and the position and orientation of the portable unit, and registering the model with the reference coordinate system at least based on the position related information respective of the at least one marker in the reference coordinate system, and based on a location of the at least one marker in the coordinate system associated with the model. The method also includes the procedure of displaying registration related information. At least one of the registration related information and a display location of the registration related information is related to the position and orientation of the portable unit in the reference coordinate system.

BRIEF DESCRIPTION OF THE DRAWINGS

The disclosed embodiments will be understood and appreciated more fully from the following detailed description taken in conjunction with the drawings in which:

FIGS. 6A, 6B, 6C and 6D are schematic illustrations of an exemplary registration process where registration related information is displayed to the user, during the registration process, in accordance with another embodiment;

FIGS. 8A-8H are schematic illustrations of an exemplary designation process where markers are designated with a designation symbol located on a visor of a HMD, in accordance with another embodiment;

FIGS. 12A and 12B are schematic illustrations of an exemplary standard marker;

DETAILED DESCRIPTION OF THE EMBODIMENTS

Figure 1A:
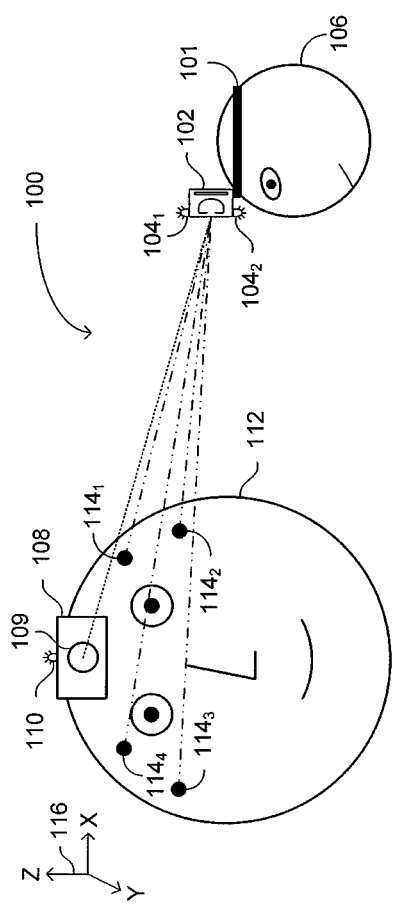
FIGS. 1A, 1B and 1C are schematic illustrations of an exemplary method for determining the location of fiducial markers located on an object, in accordance with an embodiment.

The disclosed embodiments can overcome the disadvantages of the prior art by providing a novel system and method for registering a model of an object with a reference coordinate system associated with a tracking system. The tracking system may be an optical tracking system, an electro-magnetic tracking system, an ultrasonic tracking system, an optical Time-Of-Flight tracking system. According to at least some of the disclosed embodiments, the tracking system tracks the position and orientation of a portable unit in the reference coordinate system. The portable unit includes an optical detection assembly (e.g., sensor array camera, a Position Sensitive Device—PSD, a stereoscopic camera or a Time-Of-Flight—TOF camera). Prior to the registration process a model of the object (e.g., a 2D or a 3D image of the head of the patient) is determined. Furthermore, the locations of at least three markers (i.e., fiducials or anatomical landmarks) are determined in the coordinate system associated with the model. Markers may be artificial markers that are adhered to the patient before scanning by an imaging device (e.g. CT, MRI) and can be identified in the resulting 3D imaging dataset (e.g., radio opaque fiducials in case of CT imaging). Typically artificial markers such as fiducial markers have a well-defined center (e.g., a center of a ring-shaped fiducial), and can be associated with a location in both the 3D dataset and a reference coordinate system. In general, the artificial marker can be of any shape as long as the artificial marker can be identified and associated with a location in both the 3D dataset and a reference coordinate system (e.g. not necessarily the same location in both, but the relative position of the two locations is known). For instance the markers can include a unique visual identifier employed for automatic detection and localization (i.e., determining a location) in an acquired image of the patient (e.g., ArUco markers which include a binary matrix symbol). The markers may also be anatomical landmarks (e.g., the nose bridge or the tragus in the ear). A marker may also be anatomical three dimensional surfaces (e.g., a forehead and temples of a face). Anatomical landmarks are also referred to herein as 'anatomical markers' and anatomical three dimensional surfaces are also referred to herein as 'surface markers'. In the case of surface markers, at least one surface is determined in the coordinate system associated with the model. The term 'location' relates to location coordinates of a point. Location coordinates are, for example, X, Y, Z in a 3D coordinate system such as a reference coordinate system or a 3D model coordinate system. Location coordinates may also be X, Y in a 2D coordinate system such as a 2D image coordinate system.

During the registration process, in order to determine the location of fiducial markers in the reference coordinate system, the portable unit is held at a distance from the object. The user moves the portable unit around the object through at least one registration positions. Each registration position is associated with a respective viewing angle of the fiducial. For example when the optical detection assembly of the portable unit includes an optical detector (e.g., sensor array camera or a PSD), then, the number of registration positions is at least two. When the optical detection assembly of the portable unit includes a stereoscopic camera or a TOF camera, the number of registration positions is at least one. For each registration position, the tracking system determines the position and orientation (P&O) of the portable unit in the reference coordinate system. Substantially simultaneously therewith, for each registration position, the tracking system determines position related information respective of each fiducial according to the acquired image of the fiducial. When the portable unit includes an optical detector (e.g., Charged Coupled Device—CCD camera or a Complementary Metal Oxide Semiconductor—CMOS camera or a PSD), the position related information includes a respective direction toward each of the at least one fiducial marker located on the object. Each direction defines a line in the reference coordinate system. The intersection of the at least two lines associated with each fiducial (i.e., a line for each registration position), defines the location of that fiducial in the reference coordinate system. When the portable unit includes, for example, a stereoscopic camera or a TOF camera, the position related information may be related directly to the position of the fiducial in the reference coordinate system (e.g., two directions from the two detectors in the stereoscopic camera or pixel depth information from the TOF camera). Also, the location of the markers (i.e., either of the fiducial markers or of the anatomical landmarks) may be determined with a pointer which is tracked in the reference coordinate system. Since the coordinates of the markers in the coordinate system associated with the model are known, the system can determine the correspondence between the location of the markers in the referenced coordinate system and the location of the markers in the model coordinate system. Thus, registration between the coordinate system associated with the model and the coordinate system associated with the tracking system is achieved. Furthermore, the portable unit may include a display. Also, herein, the term 'located marker' refers to a marker that the position thereof in the reference coordinate system was determined.

When the tracking system is an optical tracking system, the tracking system may exhibit an in-out configuration, an in-out-out-in configuration or an out-in configuration. In the in-out configuration, the portable unit includes at least one optical detector, and a reference unit, which is at a fixed position and orientation relative to the object being tracked, includes at least three light emitters. In the out-in configuration the portable unit includes at least three light emitters, and a reference unit includes at least one optical detector. In the in-out-out-in configuration the optical tracking system includes at least two optical detectors, one located on the portable unit and the other is located on a reference unit. Further in the in-out-out-in configuration, at least one light emitter is located on one of the portable unit and the reference unit and at least two light emitters are located on the other one of the portable unit and the reference unit (i.e., a total of at least three light emitters are employed). In both the in-out configuration and the in-out-out-in configuration, an optical detector may be located on the portable unit and employed for both tracking and marker detection (i.e., during the registration process).

In a tracking system employed for registration according to some embodiments, the position and orientation of the reference unit are fixed relative to a patient body part. For example, the reference unit is directly fixed to the patient body part. According to another example, the patient body part is fixed and the reference unit is also fixed, thus the reference unit is at fixed position and orientation relative to the patient body part without being attached thereto. At least some embodiments may also be employed in other augmented reality scenarios.

In at least some of the embodiments described herein, the tracking system can be an independent system that includes a processor and provides the system, which comprises the portable unit, with the P&O of the portable unit and the P&O of a tracked tool (e.g. when applicable). Alternatively, the tracking system can be integrated with the system (i.e., which comprises the portable unit) and P&Os can be determined by the processor of the system based on data received from the tracker units. In general, any configuration in which P&Os are provided to the system is possible.

Initially, prior to the registration procedure, a model of the patient is determined. This model may be, for example, a two-dimensional or three-dimensional image of a region of interest of the body of the patient (e.g., X-ray image, computed tomography—CT image, Magnetic Resonance Imaging—MRI image, ultrasound image, Proton Emission Tomography—PET image and the like), also referred to herein as "2D dataset" or "3D dataset" respectively. The model may be acquired pre-operatively or intra-operatively. The model includes representations of the at least three markers, which are employed as location points of reference during registration of the coordinate systems. As mentioned above, these markers may be artificial markers (i.e., fiducials) which are attached to the patient prior to the acquisition of the model and remain attached to the patient until and during the registration procedure and optionally during the medical procedure which follows. Typically the locations of the fiducials on the patient are marked with respective pen marks at the time of model acquisition, and the pen marks can be employed during the registration process (e.g., in case the fiducial falls off or moves). Alternatively or additionally the markers may be anatomical landmarks which are visible in the model (e.g., the nose bridge or the tragus in the ear). The location coordinates of these markers in the model coordinate system are determined by employing image processing techniques or by manual localization on the image (e.g., with the aid of a cursor). As described herein above, each point-like marker is associated with a respective location in the model coordinate system. For example, when the marker is a corner of an eye, the location respective of such a marker is the location of the corner of the eye. According to another example, when the marker is a ring shaped fiducial, the location respective of such a marker is the location of the intersection point between the ring axis normal to the ring plane, and the skin of the patient (e.g., as seen in the 3D dataset). As mentioned above, the marker may additionally or alternatively be a surface marker. Surfaces can be represented in various ways. For example, a surface can be represented as a group of points where each point is associated with a respective location in the model coordinate system. As a further example, a surface may be represented as a mesh of triangles. Each triangle can be defined by a vector normal to that triangle. In both examples, each surface point, as defined by the group of points or the mesh of triangles, is associated with a location in the model coordinate system. As such, a surface marker is associated with multiple locations.

Figure 1B:
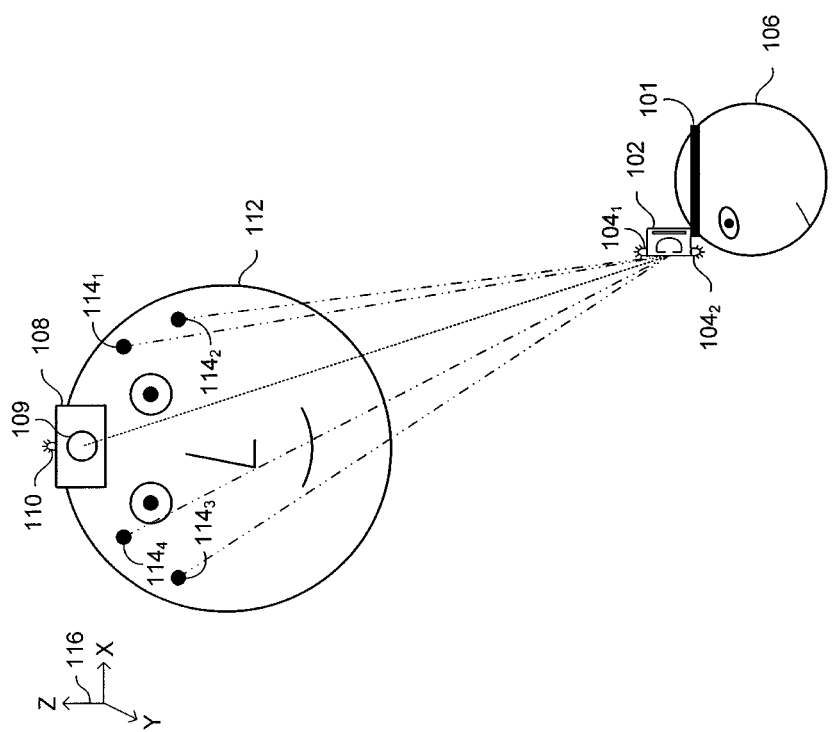
Figure 1C:
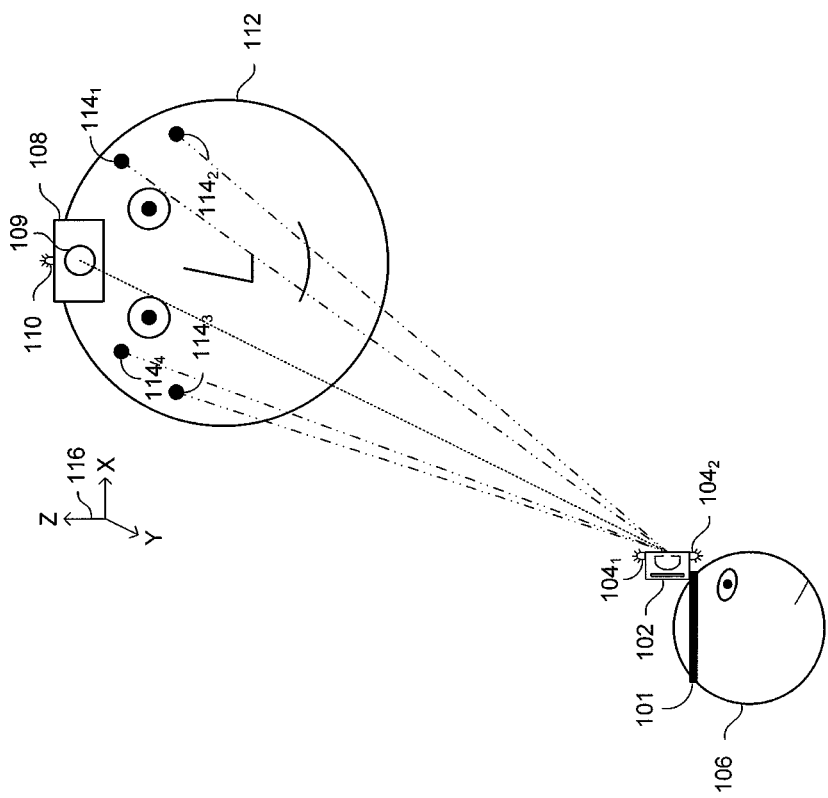

Thereafter, and prior to the medical procedure, the locations of the markers in the reference coordinate system associated with the tracking system are determined. Reference is now made to FIGS. 1A, 1B and 1C which are schematic illustrations of an exemplary method for determining the location of fiducial markers located on an object for the purpose of registering the coordinate system associated with a model of the object, with a coordinate system associated with a tracking system, generally referenced 100, in accordance with an embodiment. Tracking system 100 in FIGS. 1A, 1B and 1C is an optical tracking system which exhibits an in-out-out-in configuration. System 100 includes a reference unit 108 and a portable unit 101. In FIGS. 1A-1C portable unit 101 is a head mounted unit. Portable unit 101 includes a moving optical detector 102 associated with two light emitters 104$_1$ and 104$_2$. Reference unit 101 is located, for example, on the head of a user 106. Reference unit 108 includes a reference optical detector 109 associated with a light emitter 110. Reference unit 108, and thus light emitter 110 and optical detector 109 are in a fixed position and orientation relative to a body part of patient 112. In FIGS. 1A-1C reference unit 108 is located on the head of patient 112. In general, reference unit 108 may be fixed relative to the body part of the patient without being physically attached thereto. In other words reference unit 108 and the body part of patient 112 do not move one with respect to the other. In the example set forth in FIGS. 1A-1C optical detector 109 is a sensor array camera or a PSD. Thus, at least two registration positions are required.

To register the coordinate system associated with the model, with the coordinate system associated with the tracking system, the locations of the markers in the coordinate system associated with the tracking system should be determined. To that end, the tracking system is employed when determining the location of the markers in a reference coordinate system. Accordingly, with reference to FIG. 1A, user 106 views patient 112 from a first registration position. Moving optical detector 102 detects light emitter 110 and markers $114_1$, $114_2$, $114_3$ and $114_4$. Reference optical detector 109 detects light emitters $104_1$ and $104_2$. The processor determines the relative position and orientation between moving optical detector 102 and reference optical detector 109 at this first registration position, and thus the relative position and orientation between portable unit 101 and reference unit 108 in reference coordinate system 116. Reference coordinate system 116 is associated with reference unit 108. Furthermore, the processor determines a first direction from moving optical detector 102 toward each of markers $114_1$, $114_2$, $114_3$ and $114_4$, relative to moving optical detector 102, according to the representations of markers $114_1$, $114_2$, $114_3$ and $114_4$ detected by moving optical detector 102, as explained below.

With reference to FIG. 1B, user 106 views patient 112 from a second registration position. Moving optical detector 102 detects light emitter 110 and markers $114_1$, $114_2$, $114_3$ and $114_4$ from this second registration position and reference optical detector 108 detects light emitters $104_1$ and $104_2$ again. The processor determines the relative position and orientation between first detector 102 and reference unit 108 at this second registration position, and thus the relative position and orientation between portable unit 101 and reference unit 108, in reference coordinate system 116. Furthermore, the processor determines a second direction from moving optical detector 102 toward each of markers $114_1$, $114_2$, $114_3$ and $114_4$, relative to moving optical detector 102 according to the representations of markers $114_1$, $114_2$, $114_3$ and $114_4$ detected by moving optical detector 102.

With reference to FIG. 1C, user 104 views patient 112 from a third registration position. Moving optical detector 102 detects yet light emitter 110 and markers $114_1$, $114_2$, $114_3$ and $114_4$ from this third registration position and reference optical detector 108 detects light emitters $104_1$ and $104_2$ yet again. The processor determines the relative position and orientation between first detector 102 and reference unit 108 at this third registration position, and thus the relative position and orientation between portable unit 101 and reference unit 108, in reference coordinate system 116. Furthermore, the processor determines a third direction from moving optical detector 102 toward each of markers $114_1$, $114_2$, $114_3$ and $114_4$, relative to moving optical detector 102 according to the representations of markers $114_1$, $114_2$, $114_3$ and $114_4$ detected by moving optical detector 102.

The processor determines the location of each of markers $114_1$, $114_2$, $114_3$ and $114_4$ in reference coordinate system 116, according to the three directions associated with each one of marker $114_1$, $114_2$, $114_3$ and $114_4$. For example each direction defines a line in reference coordinate system 116 and the intersection of these three lines, associated with each marker, defines the location of that marker in reference coordinate system 116. In practice, the three lines may not intersect due to measurement errors and noise. Thus, for example, the point in space which exhibits the minimum sum of distances from the three lines is determined as the location of the marker. Alternatively, for example, each determined direction may be associated with a Figure Of Merit (FOM) and each direction is weighted according to the FOM thereof.

The above description in conjunction with FIGS. 1A-1C described registering the coordinate system associated with the model, with the coordinate system associated with the tracking system by employing three different registration positions. However, in general, two registration positions are sufficient to determine the position of the markers in the reference coordinate system. Nevertheless, in practice, more than two registration positions are employed. For example, the registration system automatically selects a plurality of discreet points in time (e.g., according to how fast the user is moving), determines the position and orientation of the user in those points in time and determines a direction for each identified fiducial as described above. It is also noted that the portable unit may include two optical detectors directed substantially toward the same Field Of View (e.g., stereoscopic camera). Consequently, detecting a fiducial with each of the two detectors is sufficient from a single user position (i.e., assuming the fiducials are detected substantially simultaneously). Then, the system may triangulate the detected fiducial in order to determine the location thereof in the referenced coordinate system.

Described hereinabove is registration based on determining the 3D locations of at least three point-like markers in a reference coordinate system, and using the known 3D locations of the markers both in the reference coordinate system and the model coordinate system to determine the registration therebetween. In case of point-like markers, the location of the marker can be the position related information respective of that marker. Registration can also be determined based on position related information other than location. Such position related information respective of point-like markers, may be for example, a vector for each marker that defines a line in the reference coordinate system. The position related information may be acquired from one or more registration positions. With regards to a surface marker, the position related information can be the surface (as describe above) as defined in the reference coordinate system. Similar to point-like markers, the surface can be acquired from one or more registration positions. For both point-like markers and surface markers, registration may be determined based on position related information acquired from a single registration position (e.g. in the case of point-like markers, position related information respective of at least three point-like markers is required). In practice, position related information can be acquired from more than one registration position. Furthermore, the above description in conjunction with FIGS. 1A-1C relates to fiducial markers (i.e., at least one of the markers is a passive or an active fiducials as further explained below), and the fiducial emits light (i.e., the fiducial incudes either a light source or a light reflector) which can be detected by the optical detector in addition to being detected by the imaging machine, as further explained below.

A method similar to the method described in conjunction with FIGS. 1A-1C can be employed, additionally or alternatively, when the markers are anatomical markers or when the artificial markers (e.g. fiducials) do not include a light source or a dedicated light reflector, and also when the optical detection assembly of the portable unit is not part of the tracking system. For example, when the optical detection assembly includes a camera, locations of anatomical and/or artificial markers can be determined by image processing algorithms that process images acquired by the camera, as further elaborated below.

The location of all or some of the markers (i.e., either fiducial markers or anatomical landmarks) may also be determined by employing a tracked pointer, as further explained below. For example, the user places the tip of the pointer on the marker and the tracking system determines the location of the tip of the pointer in the reference coordinate system (i.e., similar to as performed in manual registration). It is noted that if only a tracked pointer is employed to determine the location of the markers, than the portable unit need not include an optical detection assembly. Since the locations of the markers in the model coordinate system are known, the system can determine the correspondence between the location of the marker in the referenced coordinate system and the location of the markers in the model coordinate system. When a tracked pointer is employed, the portable unit does not need to move through registration positions as explained above.

Also, the description above referred to locations of markers. Location is a specific example of position related information. Position related information also relates to a vector (which also defines a direction and/or a line) pointing toward a location respective of the marker, in the coordinate system of the imaging sensor in the optical detection assembly, and which may be converted to a vector in the reference coordinate system, as further elaborated below. Position related information may further relate to a group of locations in a coordinate system (e.g., a surface in the reference coordinate system as described above).

Figure 2:
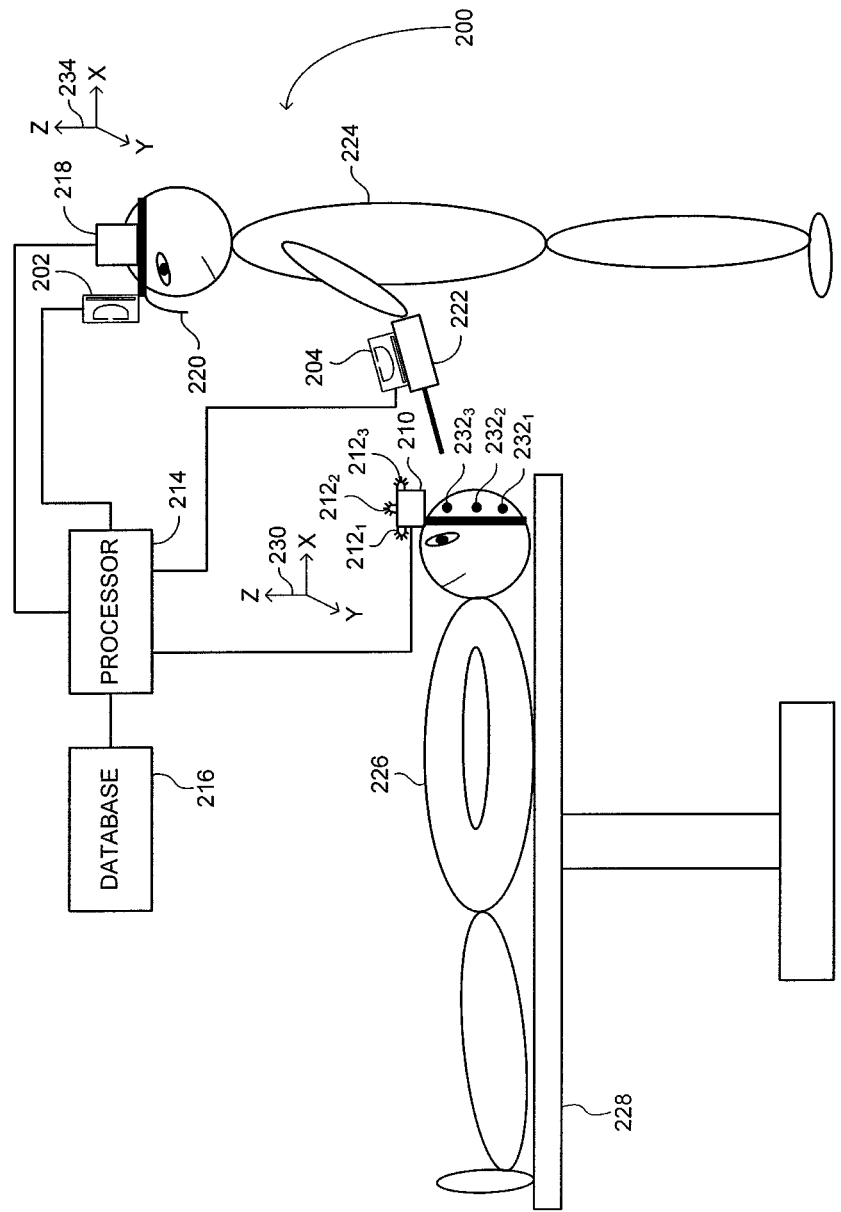
FIG. 2 is a schematic illustration of an exemplary optical tracking system for registering a coordinate system associated with a model of a patient body part with a coordinate system associated with a medical tracking system, in accordance with another embodiment.

Reference is now made to FIG. 2, which is a schematic illustration of an exemplary optical tracking system, generally reference 200, for registering a coordinate system associated with a model of a patient body part with a coordinate system associated with a medical tracking system, in accordance with another embodiment. System 200 may further be employed for tracking a medical tool in a reference coordinate system. The tool may be superimposed on a model of a patient 226. System 200 includes a first optical detector 202, a second optical detector 204 and a reference unit 210. Reference unit 210 further includes reference light emitters $212_1$, $212_2$ and $212_3$. System 200 further includes a processor 214, a database 216 and a display such as HMD 218. HMD 218 includes a visor 220. HMD 218 may also be in the form of near-eye-display. HMD 218 and first optical detector 202 define the portable unit. HMD 218 may also be replaced with a conventional screen (e.g., a hand-held tablet computer).

Processor 214 is coupled with database 216, first optical detector 202, HMD 218, second optical detector 204. When light emitters $206_1$ and $206_2$, or reference light emitters $212_1$, $212_2$ and $212_3$ are LEDs, processor 214 is optionally coupled therewith. HMD 218 along with first optical detector 202 and light emitters $206_1$ and $206_2$ is donned by a physician 224. Second optical detector 204 is attached to medical tool 222. Reference unit 210, along with reference light emitters $212_1$, $212_2$ and $212_3$ are all attached to a patient 226 body location (e.g., the head, the spine, the femur), or fixed relative thereto. Patient 226 is lying on treatment bed 228. In FIG. 2, the patient 226 body location is the head of patient 226. System 200 is associated with a reference coordinate system 230 which, in the system 200 is also the coordinate system associated with reference unit 210. In FIG. 2, the portable unit and reference unit 210 exhibit an in-out configuration. Furthermore, HMD 218 is associated with a respective coordinate system 234. Also, markers, such as markers $232_1$, $232_2$ and $232_3$, may be attached to patient 226. Although only three markers are depicted in FIG. 2, in general, similar to as described in FIGS. 1A-1C, more than three markers may be employed. Furthermore, at least one of markers $232_1$, $232_2$ and $232_3$ is a fiducial marker. Also, the remaining ones of markers $232_1$, $232_2$ and $232_3$ may be anatomical landmarks.

Processor 214 may be integrated within HMD 218 or attached to the user (e.g., with the aid of a belt or in the user's pocket). Alternatively, processor 214 may be located at a separate workstation and coupled with other system components (e.g., by wire and/or wirelessly). Medical tool 222 is, for example, a pointer employed for determining the location of the markers employed for registration. Medical tool 222 may also be an ultrasound imager, a medical knife, a catheter guide, a laparoscope, an endoscope, a medical stylus or any other tool used by a physician 224 during a procedure conducted on a patient 226. Also, the term coupled herein relates to either coupled by wire or wirelessly coupled.

In general, system 200 may be employed for registering the coordinate systems associated with a model of patient 226 with reference coordinate system 230 as well as for tracking medical tool 222. Similar to as described above, prior to registration, a model of the patient is determined which includes markers, such as marker $232_1$, $232_3$ and $232_3$. Markers $232_1$, $232_3$ and $232_3$ are employed as location points of reference during registration procedure and the location coordinates of these markers, in the model coordinate system are determined (i.e., employing image processing techniques or by manual localization on the model). This model, along with the location coordinates of the markers is then stored in database 216. Alternatively, the locations respective of the markers are determined during surgery.

The above mentioned image processing techniques include, for example, neural networks that were trained to identify specific anatomical and/or artificial markers in 3D datasets. A neural network can be trained to identify (e.g. segment and provide a marker identifier—a tag), for example, fiducials having a specific 3D shape, ears, nose or eyes. Another neural network can be trained to determine the location respective of a marker once a marker is segmented and tagged. For example, the neural network can be trained to determine the location (i.e., in the 3D dataset coordinate system) of the intersection of an axis of a ring-shaped fiducial with the surface of the skin of the patient as the location respective of the fiducial. As another example, a neural network can determine the location of the corner of the eye. The neural network can be trained to tag a detected marker and respective location, for example as "left ear", "right eye corner", "fiducial 2" and the like. Alternatively or additionally, other algorithms can also be employed to extract these locations.

Thereafter, physician 224 moves through at least two registration positions. For each registration position, first optical detector 202 detects markers $232_1$, $232_2$ and $232_3$ and light emitters $212_1$, $212_2$ and $212_3$. For each registration position, processor 214 determines the position and orientation of HMD 218 (i.e., in reference coordinate system 230), according to the detected directions of light emitters $212_1$, $212_2$ and $212_3$ and the known locations of light emitters $212_1$, $212_2$ and $212_3$ on reference unit 210 (e.g., these locations are stored in database 216). Furthermore, for each registration position, processor 214 determines a respective direction from HMD 218 toward each of markers $232_1$, $232_2$ and $232_3$. Processor 214 determines the location of each of markers $232_1$, $232_2$ and $232_3$ according to the respective directions thereof at each registration position (e.g., the intersection of the lines defined by each respective direction, defines a location point in reference coordinate system 230).

Also, physician 224 may employ a pointer to locate the markers (i.e., either the fiducial markers or the anatomical landmarks). In such a case medical tool 222 takes the form of a pointer. In order to determine the location of the markers, physician 224 places the tip of the pointer on the markers. As a further example, the user may employ a designation symbol located on visor 220 to designate the markers, as further elaborated below in conjunction with FIGS. 7A-7I and 8A-8D. Second optical detector 204 also acquires an image of light emitters $212_1$, $212_2$ and $212_3$ and processor 214 determines the location of the pointer (i.e., of medical tool 222), and thus of the marker, in reference coordinate system 230. Similar to as mentioned above, once processor 214 determines the position of the markers $232_1$, $232_2$ and $232_3$ (i.e., of the fiducials and the anatomical landmark) in reference coordinate system 230, processor 214 can register the coordinate system associated with the model of the body part of patient 226 with reference coordinate system 230.

When processor 214 determines at least an initial registration (e.g., registration with a relatively large error) the coordinate system associated with the model of the body part of patient 226 with reference coordinate system 230, processor 214 may display on visor 220 registration related information as further explained below. Once the coordinate system associated with the model of the body part of patient 226 is registered with reference coordinate system 230, tracking system 200 may be employed to track another medical tool (e.g., medical tool 222 takes the form of a needle) in reference coordinate system 230. Furthermore, tracking system can superimpose a representation of such a medical tool on the model of patient 222. Also, according to the determined relative positions and orientations between medical tool 222, HMD 218 and patient 226, and the registration between the model of patient 226 and reference coordinate system 230, processor 214 may render the model of patient 226 in the correct perspective and provide the rendered model to HMD 218. Furthermore, navigational information (e.g., a mark representing a target location, a line representing the trajectory and projected trajectory of the tool) associated with medical tool 222, may be superimposed on the model. As a further example, when medical tool 222 is an ultrasound imager, system 200 be employed for presenting data acquired by medical tool 222 at the location from which that data was acquired.

The light emitters described hereinabove in conjunction with FIGS. 1A-1C and 2 may be either active light emitters (e.g., LEDs) or passive light emitters which reflect either the ambient light or dedicated light directed thereat (e.g., the light from the LEDs located on the portable unit). The passive light emitters may be reflectors (e.g., reflective spheres) or retro-reflectors which reflect light toward the direction from which it impinged thereon. The fiducial markers described hereinabove in conjunction with FIGS. 1A-1C and 2 may also be passive fiducials or active fiducials. The passive fiducial also reflects the light impinging thereon. The active fiducial includes a LED and a battery and is activated just before the registration process starts as further explained below in conjunction with FIGS. 11C-11E and 13A.

Figure 3:
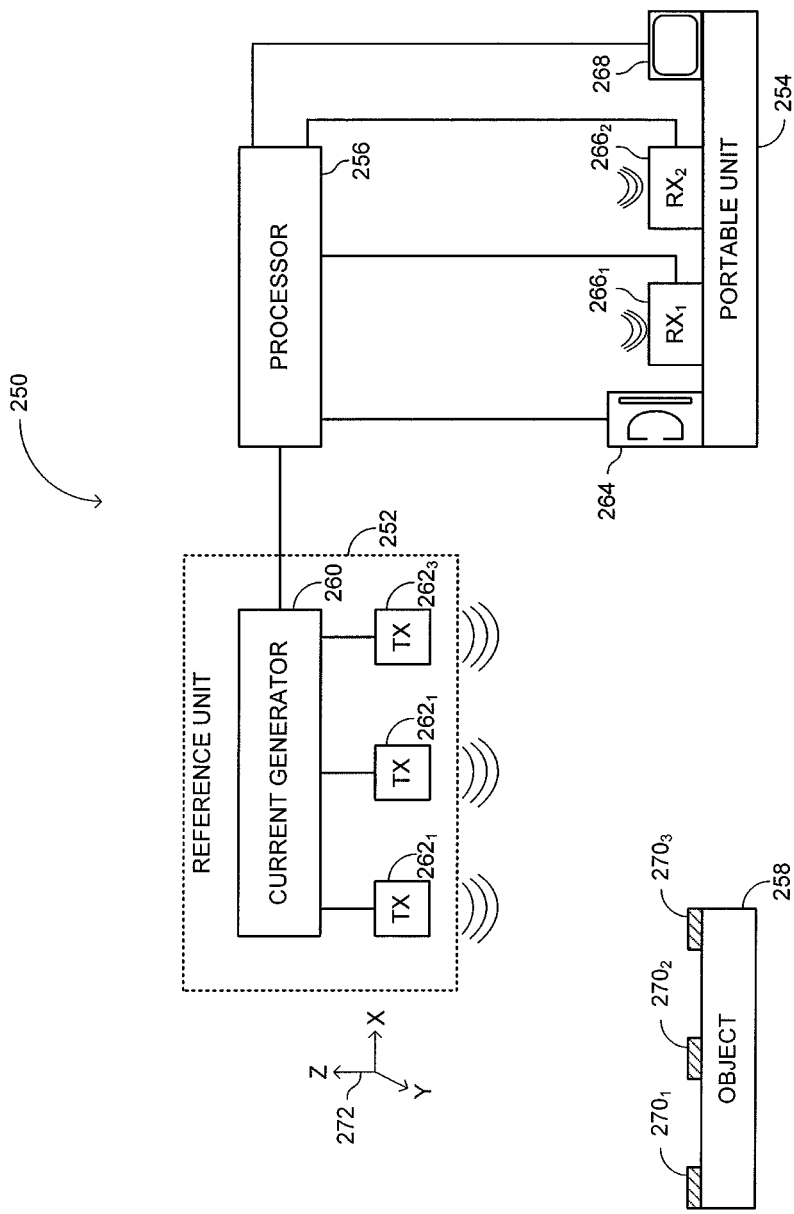
FIG. 3 is a schematic illustration of an exemplary electro-magnetic tracking system employed for registering a model coordinate system with a reference coordinate system, constructed and operative in accordance with a further embodiment.

As mentioned above, the tracking system employed for registration may also be an electro-magnetic tracking system, which tracks the location of the portable unit in a reference coordinate system. Reference is now made to FIG. 3, which is a schematic illustration of an exemplary electromagnetic tracking system, generally referenced 250, employed for registering a model coordinate system with a reference coordinate system, constructed and operative in accordance with a further embodiment. System 250 includes a reference unit 252, a portable unit 254 and a processor 256. Reference unit 252 includes a current generator 260 and magnetic field transmitting elements (e.g., coils) $262_1$, $262_2$ and $262_3$. Portable unit 254 includes an optical detection assembly 264 and magnetic field receivers $266_1$ and $266_2$. Portable unit 254 also includes a display 268. Portable unit 254 may be embodied as an HMD similar to HMD 218 (FIG. 2) or a hand held unit (e.g., a hand-held tablet computer). Optical detection assembly 264 is for example sensor array camera, a PSD, a stereoscopic camera a TOF camera.

Processor 256 is coupled with magnetic current generator 260, with optical detection assembly 264, with magnetic field receivers $266_1$ and $266_2$ and with display 268. System 250 aims to register the coordinate system associated with a model of object 258 with reference coordinate system 272. Object 258 includes at least three markers $270_1$ $270_2$ and $270_3$. At least one of markers $270_1$ $270_2$ and $270_3$ is a fiducial marker. In system 250, the position and orientation of reference unit 252 are fixed relative to object 258. For example, reference unit 252 is directly fixed to object 258. Alternatively, object 258 is fixed and reference unit 258 is also fixed. Thus, reference unit 252 is at fixed position and orientation relative to object 258 without being attached thereto. Alternatively, at least two additional magnetic field receivers (not shown) are attached to object 258. Thus, processor 256 can determine relative position and orientation between reference unit 252 and object 258.

Similar to as described above in conjunction with FIGS. 1A-1C and 2, a user (not shown) moves portable unit 254 through at least two registration positions. For each registration position processor 256 determines the position and orientation of portable unit 254 in reference coordinate system 272 according magnetic field transmitted by transmitting elements $262_1$, $262_2$ and $262_3$ and received by magnetic field receivers $266_1$ and $266_2$. For each registration position, optical detection assembly 264 acquires an image of the fiducial ones of markers $270_1$ $270_2$ and $270_3$. For each registration position processor 256 determines a respective direction toward each of the fiducial ones of markers $270_1$ $270_2$ and $270_3$, relative to optical detection assembly 264, according to the image acquired by optical detection assembly 264. Each direction defines a line in reference coordinate system 272 and the intersection of the three lines, associated with each marker, defines the location of that marker in reference coordinate system. A user may also employ a tracked pointer (not shown) to determine the location of markers $270_1$ $270_2$ and $270_3$. Since the coordinates of the markers $270_1$ $270_2$ and $270_3$ in the coordinate system associated with the model are known, system 250 can determine the correspondence between the location of markers $270_1$ $270_2$ and $270_3$ in the referenced coordinate system 272 and the location of the markers in the model coordinate system. Thus, registration between the model coordinate system and reference coordinate system 272 is achieved. When processor 256 determines at least an initial registration between the coordinate system associated with the model of object 258 with reference coordinate system 272, processor 256 may display on display 268 registration related information as further explained below.

Figure 4:
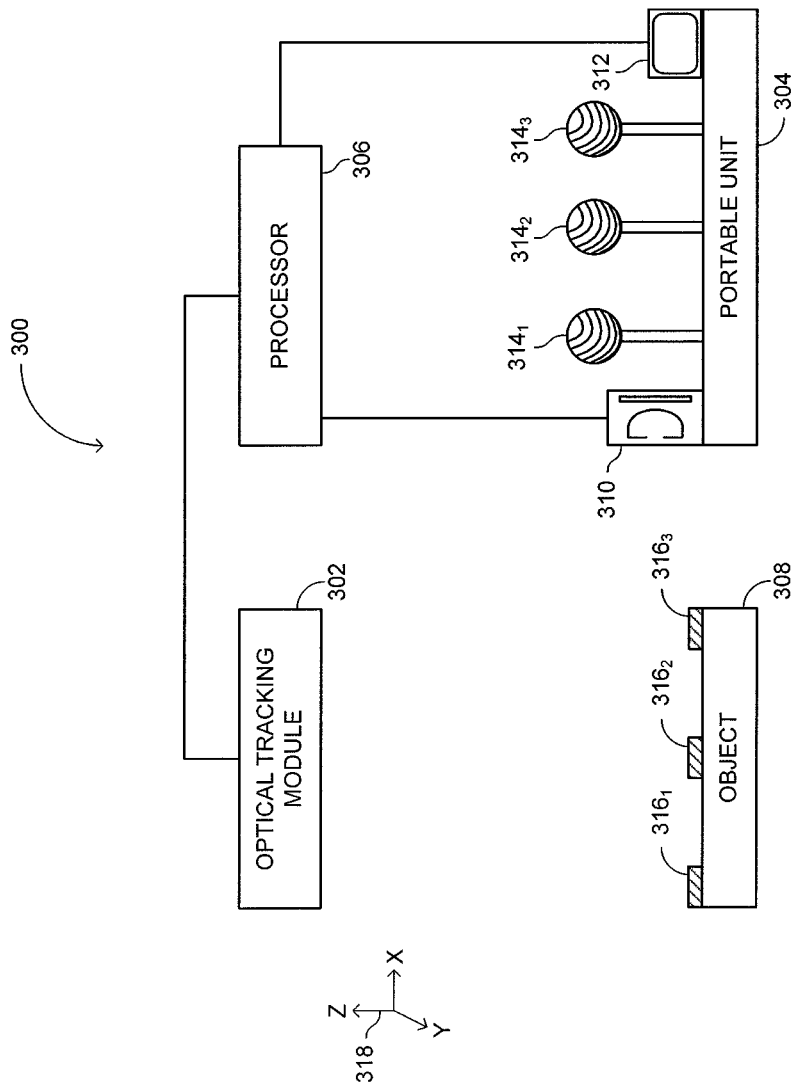
FIG. 4 is a schematic illustration of an optical tracking system which tracks the location of the portable unit in a reference coordinate system, constructed and operative in accordance with another embodiment.

Reference is now made to FIG. 4, which is a schematic illustration of an optical tracking system, generally referenced 300, which tracks the location of the portable unit in a reference coordinate system, constructed and operative in accordance with another embodiment.

System 300 includes an optical tracking module 302, a portable unit 304 and a processor 306 which exhibits the out-in configuration. Portable unit 304 includes an optical detection assembly 310 and at least three light emitters $314_1$ $314_2$ and $314_3$. Portable unit 304 also includes a display 312. In FIG. 4, light emitters $314_1$ $314_2$ and $314_3$ take the form of reflective spheres which reflect light impinging thereon. Optical detection assembly 310 is for example sensor array camera, a PSD, a stereoscopic camera or a TOF camera.

Processor 306 is coupled with optical tracking module 302, with optical detection assembly 310 and with display 312. System 300 aims to register the coordinate system associated with a model of object 308 with reference coordinate system 318. Object 308 includes at least three markers $316_1$ $316_2$ and $316_3$. At least one of markers $316_1$ $316_2$ and $316_3$ is a fiducial marker. In system 300, the position and orientation of reference unit optical tracking module 302 are fixed relative to object 308.

Optical tracking module 302 may be embodied as a stereoscopic camera (i.e., two cameras, directed toward substantially the same Field Of View and exhibiting a fixed and known relative position and orientation between the two cameras). Alternatively, optical tracking module 302 may be embodied as a Time-Of-Flight (TOF) camera which includes a light emitter which emits modulated light (e.g. continuous wave modulated light or pulsed modulated light) and an optical detector. When optical tracking module 302 is embodied as a stereoscopic camera, processor 306 determines the location of each one of light emitters $314_1$ $314_2$ and $314_3$ using triangulation. Thus, processor 306 can determine the position and orientation of portable unit 304 in reference coordinate system 318. When optical tracking module 302 is embodied as a TOF camera, each image includes the depth information of each pixel (i.e., the distance between the TOF camera and the object being imaged) and each pixel provides the direction from the TOF camera toward the object being imaged. Thus, an image of light emitters $314_1$ $314_2$ and $314_3$ includes information relating to the location of these light emitters in reference coordinate system 318. Thus, processor 306 can determine the position and orientation of portable unit 304 in reference coordinate system 318.

Optical detection assembly 310 provides information relating to directions from an imaging sensor of optical detection assembly 310, toward each one of markers $316_1$ $316_2$ and $316_3$ (e.g., which are point-like markers) in the sensor coordinate system. For example, when optical detection assembly 310 is a pixel array camera, a stereoscopic camera or a TOF camera, optical detection assembly 310 includes one or two imaging sensors (e.g., CCD sensor, CMOS sensor), where each imaging sensor can generate an image that is associated with a 2D coordinate system. Each 2D location in the image 2D coordinate system is associated with a respective vector in the sensor 3D coordinate system based on a predetermined sensor calibration. The locations in the image 2D coordinate system can be provided in sub-pixel resolution (i.e., not necessarily an integer location).

Optical detection assembly 310 acquires an image or images of markers $316_1$ $316_2$ and $316_3$. Processor 306 identifies markers $316_1$ $316_2$ and $316_3$ in the acquired image or images and determines a location for each of markers $316_1$ $316_2$ and $316_3$ in the image 2D coordinate system, for example, using image processing techniques or neural networks. According to one example, when markers $316_1$ $316_2$ and $316_3$ are fiducials including LEDs, then markers $316_1$ $316_2$ and $316_3$ are identified and localized using for example Binary Large Object (BLOB) analysis. When the markers $316_1$ $316_2$ and $316_3$ are, for example, ring-shaped fiducials, image segmentation or neural networks can be employed to identify the markers $316_1$ $316_2$ and $316_3$ in the acquired image or images. When the markers $316_1$ $316_2$ and $316_3$ include, for example, visible markings such as ArUco markers, image processing algorithms can detect these markers in the image and determine their location. Thereafter, processor 306 can determined a vector in the sensor coordinate system pointing toward locations respective of markers $316_1$ $316_2$ and $316_3$. Since the fixed alignment between the sensor or sensors and portable unit 304 is known (i.e., the alignment between a coordinate system of the sensor and a coordinate system of portable unit 304), the respective vectors are also known in the coordinate system associated portable unit 304. Based on P&O of portable unit 304 in reference coordinate system 318, the vectors pointing to toward locations respective of markers $316_1$ $316_2$ and $316_3$ in reference coordinate system 318 are also known. These vectors in reference coordinate system 318 are the respective position related information of each of markers $316_1$ $316_2$ and $316_3$.

When optical detection assembly 310 is a camera, processor 306 determines a respective vector pointing toward a location respective of each of markers $316_1$ $316_2$ and $316_3$. When optical detection assembly 310 is stereoscopic camera, processor 306 determines two respective vectors pointing toward respective locations of each of markers $316_1$ $316_2$ and $316_3$. When optical detection assembly 310 is a TOF camera, processor 306 determines a respective vector pointing toward a location respective of each of markers $316_1$ $316_2$ and $316_3$ and a respective distance to each of markers $316_1$ $316_2$ and $316_3$. When optical detection assembly 310 includes a PSD, the PSD generates respective signals indicative of the direction from which light, originating for LEDs markers $316_1$ $316_2$ and $316_3$, is received. Processor 306 determines a respective vector toward a location respective of each of markers $316_1$ $316_2$ and $316_3$ from these respective signals.

In the examples above, the location determined from the image can be a location that is different from the location of the respective marker in the 3D dataset. However the relative position between the two locations is known. In such cases, the processor can determine a location that corresponds to the marker location in the 3D dataset based on this known relative position. For example, an artificial marker can include both a radio-opaque fiducial and an ArUco marker, where the relative position between the two is known. As such, once the location and orientation of the ArUco marker in the reference coordinate system is determined (e.g. from the acquired image and corresponding P&O of the portable unit), the location of the radio-opaque fiducial in the reference coordinate system can also be determined and used as the position related information respective of the artificial marker. Alternatively, the registration algorithm is provided, for each marker, with both the location of the radio-opaque fiducial in the 3D dataset and the position related information respective of the ArUco marker, and uses the known relative position between the two when determining the registration.

The description above referred to point-like markers. Nevertheless, the above applies to surface markers as well. This surface representation is acquired, for example, by employing a tracked TOF camera, a tracked structured light scanner, a tracked stereoscopic camera or a laser scanner which provides 3D information. Such a surface representation is also referred to herein as a 'surface scan'. For example, a TOF camera provides distance and direction information for each pixel in the image. A stereoscopic camera provides two directions for corresponding pixels in the stereoscopic image pair (e.g. pixels in both images representing the same point in the surgical field) from which the location of these pixels can be derived relative to the stereoscopic camera. A structured light scanner provides information regarding the topology of the surface being imaged. In general, the surface representation can be acquired by any sensor using any 3D surface acquisition techniques. The processor can define the surface in a sensor coordinate system. Given the P&O of the portable unit, the processor can define the surface in the reference coordinate system. Herein, with regards to either point-like markers or surfaces, the term 'marker representation' relates to the representation of a marker in a 3D dataset. The term 'representation of a marker' relates to, an image, images, or 3D information acquired by an optical detection assembly, or to information extracted from such image or images or 3D information (e.g., information relating to BLOBs).

Similar to as described above in conjunction with FIGS. 1A-1C and 2, a user (not shown) moves portable unit 304 through at least two registration positions. For each registration position processor 306 determines the position and orientation of portable unit 304 in reference coordinate system 318 according to the images acquire by optical tracking module 302. For each registration position, optical detector 304 acquires an image of the fiducial ones of markers $316_1$, $316_2$ and $316_3$. For each registration position, processor 306 determines a respective direction toward the fiducial ones of markers $316_1$, $316_2$ and $316_3$, relative to optical detection assembly 310, according to the image acquired by optical detection assembly 310. Each direction defines a line in reference coordinate system 318 and the intersection of the two lines, associated with each marker, defines the location of that marker in reference coordinate system. The user may alternatively employ a tracked pointer to determined location of markers $316_1$, $316_2$ and $316_3$. Since the coordinates of the markers $316_1$, $316_2$ and $316_3$ in the coordinate system associated with the model are known, system 30 can determine the correspondence between the location of markers $316_1$, $316_2$ and $316_3$ in the referenced coordinate system 318 and the location of the markers in the model coordinate system. Thus, registration between the model coordinate system and reference coordinate system 318 is achieved. When processor 306 determines at least an initial registration between the coordinate system associated with the model of object 308 with reference coordinate system 318, processor 306 may display on display 268 registration related information as further explained below.

Figure 5:
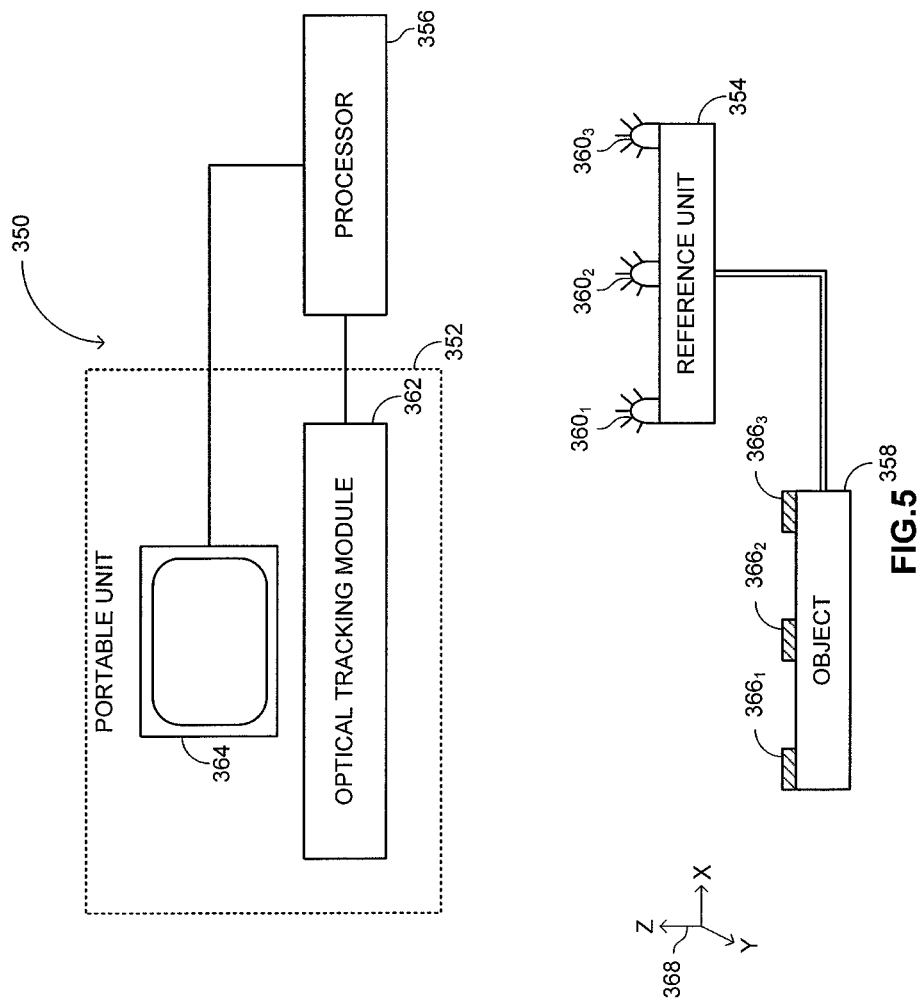
FIG. 5 is a schematic illustration of an optical tracking system, which tracks the location of the portable unit in a reference coordinate system, constructed and operative in accordance with a further embodiment.

Reference is now made to FIG. 5, which is a schematic illustration of an optical tracking system, generally referenced 350, which tracks the location of the portable unit in a reference coordinate system, constructed and operative in accordance with a further embodiment. System 350 includes a portable unit 352, a reference unit 354 and a processor 356. Portable unit 352 includes an optical tracking module 362 coupled with processor 356. Portable unit 352 further includes a display also coupled with processor 356. Reference unit 354 includes at least three light emitters $360_1$, $360_2$ and $360_3$ and is attached to object 358. In the example brought forth in FIG. 5, light emitters $360_1$, $360_2$ and $360_3$ are LEDs. Object 358 includes three markers $366_1$, $366_2$ and $366_3$, one of which is a fiducial. Also, the relative position between reference unit 354 and object 358 is fixed.

Similar to optical tracking module 302 (FIG. 4), optical tracking module 362 may be embodied as a stereoscopic camera or a TOF camera. When the optical tracking module includes a stereoscopic camera or a TOF camera, a single registration position is sufficient to determine the location of markers $366_1$, $366_2$ and $366_3$ in reference coordinate system 368 (i.e., assuming all of the fiducial one of markers $366_1$ $366_2$ and $366_3$ are within the Field Of View of optical tracking module 362).

Accordingly, optical tracking module 362 acquires an image or images of light emitters $360_1$, $360_2$ and $360_3$ and processor 356 determines the location optical tracking unit 362 and consequently of portable unit 352 in reference coordinate system 368. Also, optical tracking module 362 acquires an image or images of the fiducial one of markers $366_1$, $366_2$ and $366_3$, and processor 356 determines the location of markers $366_1$, $366_2$ and $366_3$ relative to optical tracking module 362. Since processor 356 determined the location of optical tracking unit 362 in reference coordinate system 368, processor 356 can determine the location of the fiducial ones of markers $366_1$, $366_2$ and $366_3$ in reference coordinate system 368. The user may alternatively employ a tracked pointer (e.g., tracked in a coordinate system associated with portable unit 352) to determined location of markers $366_1$, $366_2$ and $366_3$. Since the coordinates of the markers $366_1$, $366_2$ and $366_3$ in the coordinate system associated with the model are known, system 360 can determine the correspondence between the location of markers $366_1$ $366_2$ and $366_3$ in the referenced coordinate system 368 and the location of the markers in the model coordinate system. Thus, registration between the model coordinate system and reference coordinate system 368 is achieved. When processor 356 determines at least an initial registration between the coordinate system associated with the model of object 358 with reference coordinate system 368, processor 356 may display on display 268 registration related information as further explained below.

In the examples brought herein above in conjunction with FIGS. 1A-1C, 2, and 5, the optical detection assembly located on the portable unit is employed for both tracking the portable unit and for registration. However, the portable unit may include two separate optical detection assemblies, one employed for tracking the portable unit and the other employed for registration.

With respect to any of the tracking systems described hereinabove in conjunction with FIGS. 1A-1C, 2, 3, 4 and 5, during the registration process, information relating to the registration process may be displayed to the user (i.e., on the respective display associated with any one of the portable units described hereinabove in conjunction with FIGS. 1A-1C, 2, 3, 4 and 5). This registration related information may be, for example, a marker identifier (e.g., a number, a character), an indication that a marker has been identified, an indication that a marker has been located, the error associated with the determined location of the marker, a score indicating the quality of the registration (e.g., the estimated error of the registration), instructions to the user and the like. For example, once the location of a marker is determined, a marker indicator may be displayed to the user, for example, by superimposing the indicator (e.g., a circle, a square, an arrow and the like) on the marker, thus providing the user with information regarding the progress of the registration process. Each kind of marker (i.e., either fiducial or anatomical landmark) may have a corresponding indicator (e.g., a circle for fiducials and a square for anatomical landmarks). When the positions of a sufficient number of markers are determined (i.e., at least three when registering three dimensional coordinate systems) and registration is calculated, a score indicating the quality of the registration may be displayed to the user. The registration related information may further include user related information such as user selection or user guidance. For example, the user may direct the tracking system whether the score is good enough or whether to continue the registration process (e.g., by enabling the system to locate additional markers). For example, when the markers are located on both sides of the head, then the system may direct the user to physically look at the head of the patient from the other side to allow the system to identify additional markers. To improve the accuracy of the registration, the system may further guide the user to look at the head of the patient from the other side, even if the registration was already successful using markers from only one side of the head of the patient. Once an initial registration is determined (e.g., may be with a large error), the system may also direct the user (e.g., via the display) to markers that location thereof has yet to be determined or that the location thereof was determined with a large error. The system may also indicate to the user the error that each marker contributed to the final calculation of the registration. The user may also discard the use of specific markers in the calculation of the registration. Discarded markers may be indicated with a different indicator than the markers that were employed for registration (e.g., discarded markers shall be marked with a red square). For example if the user suspects that certain markers may have moved since the preoperative image has been acquired. Also, the surgeon may request that the registration be recalculated without using certain markers.

Reference is now made to FIGS. 6A, 6B, 6C and 6D, which are schematic illustrations of an exemplary registration process where registration related information is displayed to the user, for example on a visor 400, during the registration process, in accordance with another embodiment. The user observes patient 402 lying on treatment bed 404. In the example set forth in FIGS. 6A-6D, a reference unit 406 is at a fixed position and orientation relative to the head of patient 402. Reference unit 406 may be any one of the reference units described above in conjunction with FIGS. 1A-1C, 2, 3, 4 and 5. In the example brought forth in FIGS. 6A-6D, reference unit 406 includes three LEDs $408_1$, $408_2$ and $408_3$. Alternatively, reference unit may include magnetic field transmitters or receivers as explained above. Furthermore, marker $401_1$, $410_2$, $410_3$, $410_4$, $410_5$, $410_6$ and $410_7$ are on patient 402 (i.e., either fiducials or anatomical landmarks or both).

With reference to FIG. 6A, the user is located at a first registration position. At this first registration position, the user views markers $410_1$, $410_2$, $410_3$ and $410_4$. A registration system according some embodiments identifies markers $410_1$, $410_2$ $410_3$ and $410_4$ (e.g., markers $410_1$, $410_2$, $410_3$ and $410_4$ are within the field of view of an optical detector) and informs the user (e.g., by displaying text on visor 400) that four markers have been identified. Furthermore, the system (e.g., any of the systems described hereinabove) instructs the user to change the point of view thereof. It is noted that when a stereoscopic camera or a TOF camera are employed with the portable unit, the system is also able to determine the location of markers $410_1$, $410_2$ $410_3$ and $410_3$ from a single registration position.

Figure 6B:
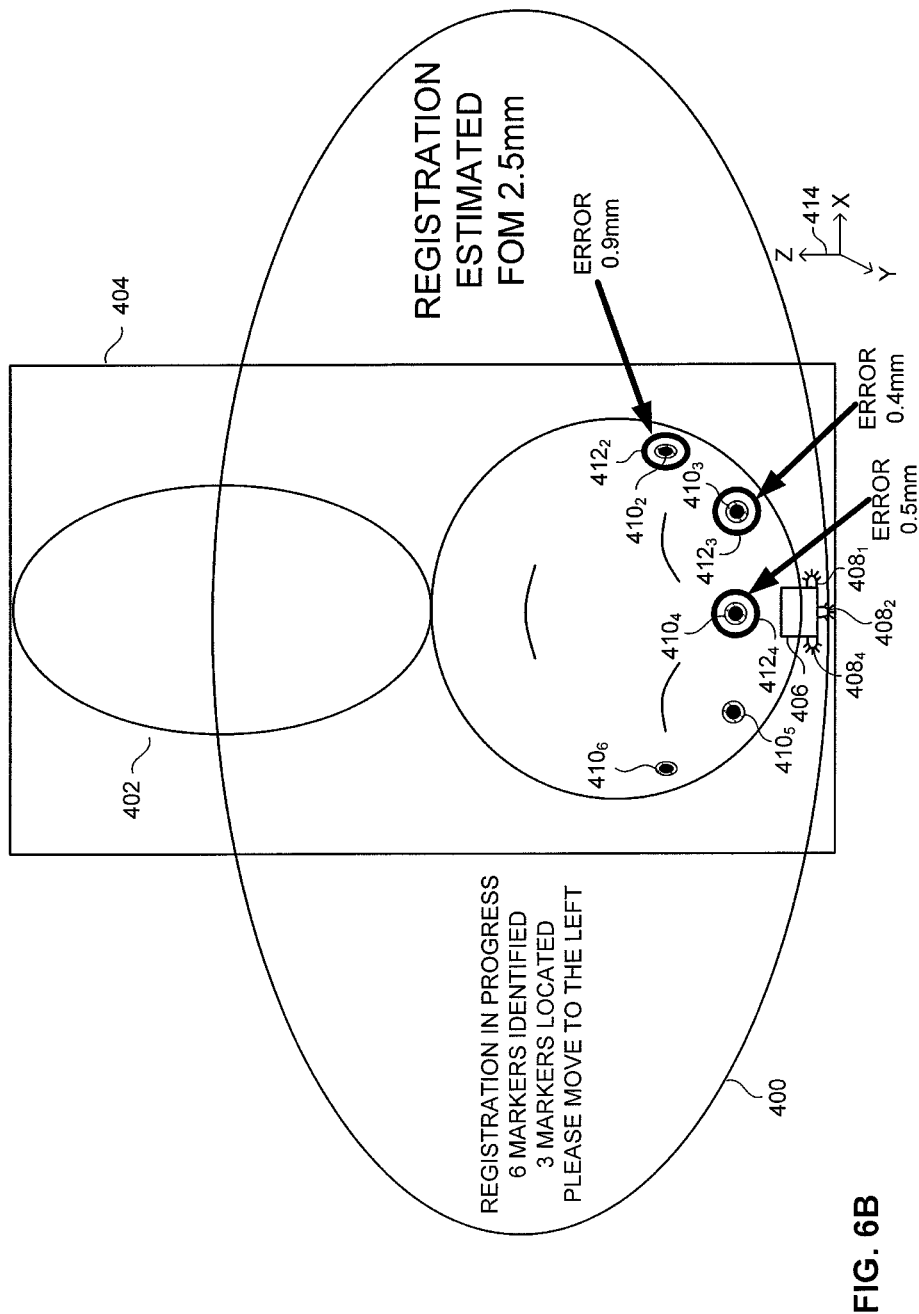
Figure 6C:
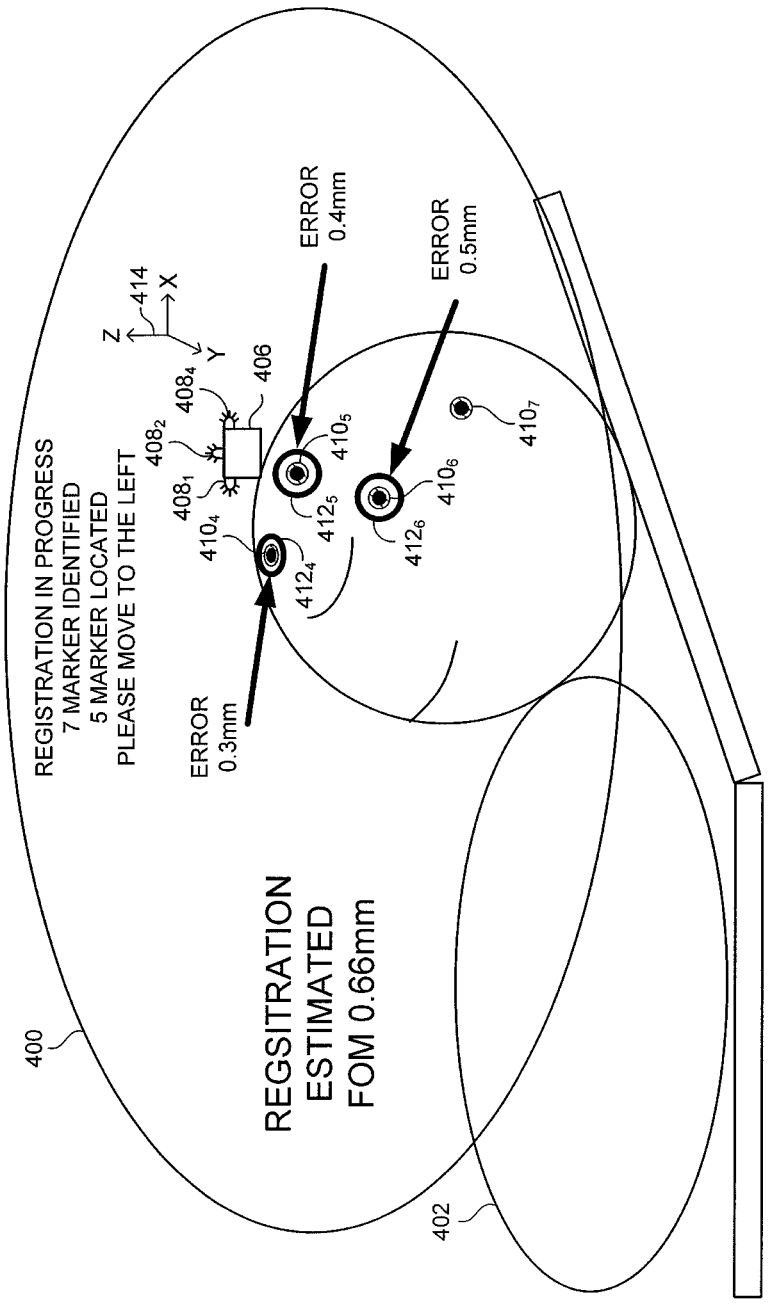
Figure 6D:
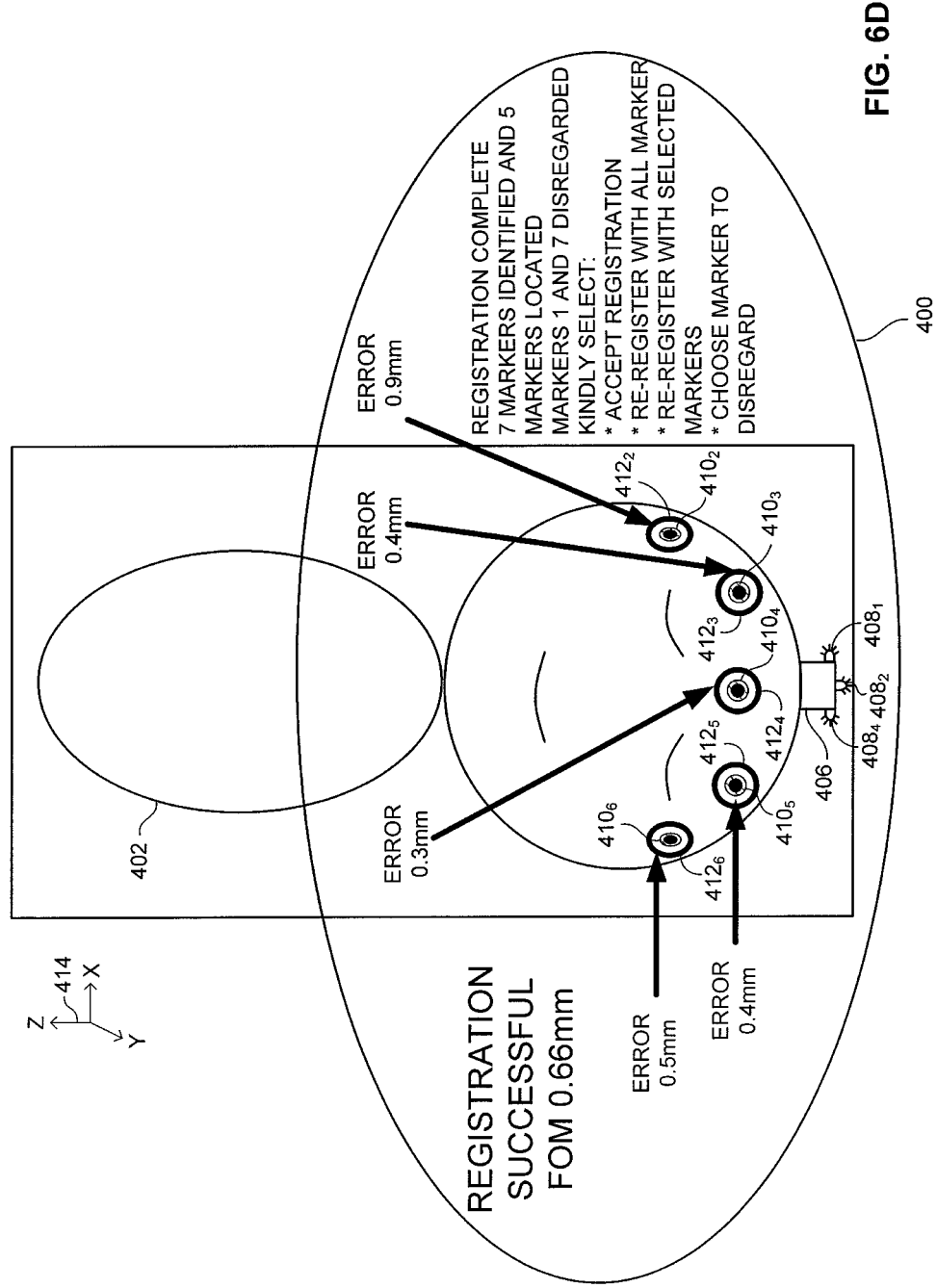

With reference to FIG. 6B, the user is located at a second registration position. At this second registration position, the user views markers $410_2$, $410_3$, $410_4$, $410_5$ and $410_6$. The registration system according to some embodiments further identifies markers $410_5$ and $410_6$ (e.g., markers $410_2$, $410_3$, $410_4$, $410_5$ and $410_6$ are within the field of view of an optical detector) and informs the user that 6 markers have been identified. Furthermore, the registration system determines the location of markers $410_2$, $410_3$ and $410_4$ and displays respective marker indicators $412_2$, $412_3$ and $412_4$ on display 400, superimposed over the respective marker thereof, as seen by the user through the transparent visor. Since the system according to some embodiments tracks a portable unit in the reference coordinate system, the system can determine the P&O of the display. Since the system also determines the location of the markers, the system can superimpose a marker indicator at the display location which is related to the position of the markers as seen on or through the display. In general, the registration system displays the registration related information at a display location which corresponds to the position and orientation of the portable unit. The registration system may display the registration related information at a display location which is related to the position of the markers. In FIGS. 6B-6D, marker indicator $412_2$, $412_3$ and $412_4$ take the form of circles. The registration system also provides the user with an indication of the error of the determined location thereof. For example, the registration system determined the position of marker $410_2$ with an error of 0.9 mm, marker $410_3$ with an error of 0.3 mm and marker $410_4$ is located with an error of 0.5 mm. It is noted that the size, color or shape of the marker indicator may be related to the error associated with the position of that marker. For example, the diameter of the circle is proportional to the location of the marker over which that circle is superimposed. Since three markers have been identified, the system can estimate the registration between the reference coordinate system and the coordinate system associated with the model of the patient. However, this registration may be an initial registration with a relatively large error (e.g., 2.5 millimeters in the example set forth in FIG. 6B). Nevertheless, since the spatial relationship (i.e., the relative position) between the markers is known, the system can instructs the user to move toward markers which are yet to be detected (i.e., in general, the registration related information includes instructions to the user). In FIG. 6B, the system informs the user that 6 markers have been identified and 3 located. Furthermore, the system displays on display 400 instructions to the user to move to the left.

With reference to FIG. 6C, the user is located at a third registration position. At this third registration position, the user views markers $410_4$, $410_5$ $410_6$ and $414_7$. The registration system according to the some embodiments further identifies marker $410_7$ (e.g., markers $410_4$, $410_5$, $410_6$ and $410_7$ are within the field of view of an optical detector). The registration system according to some embodiments determines the location of markers $410_5$ and marker $410_6$ and marks these markers with a respective circle $412_5$ and $412_6$. The system determined the position of marker $410_5$ with an error of 0.4 mm, marker $410_6$ with an error of 0.5 mm. Furthermore, the system improved the location estimation of marker $410_4$ and the location error associated with marker $410_4$ is now 0.3 mm. The system was not able to determine the location of markers $414_7$ as well as of marker $410_1$. The system also improved the registration error (e.g., 0.66 millimeters in the example set forth in FIG. 6C). The system further instructs the user to move to the left.

With reference to FIG. 6D, the registration system according to some embodiments displays on display 400 a summary of the registration process for the user and indicates that the registration is complete and the displays the registration error (i.e., the registration related information includes, for example, a summary of the registration process for the user and indicates that the registration is complete and displays the registration error). The system further displays information relating to the markers employed for registration and various options for the user to choose from. In general, as explained above, the system displays registration related information to a user at a display location related to the position and orientation of the portable unit. It is noted that since the system determines the position of the markers, the system may adjust the information displayed on the display accordingly. For example, the marker indicators may be displayed at a display location corresponding to the position of the markers as seen on or through the display, while the registration error, instructions to the user and the like may be displayed at a different selected location which does not interfere with the marker indicators. It is noted that, in general, marker indicator symbols (e.g. a circle around the marker, as described in FIGS. 6A-6D) can be displayed either once the marker location is determined or once an initial registration is determined (e.g. without first determining marker locations).

During the registration process, a segmented model of the object, generated based on the 3D dataset, may be displayed on visor 400. This segmented model may be a segmented model that includes anatomical elements (e.g., the outer surface of the head, including the eyes, the nose and the ears) and/or artificial markers that are directly visible to the user. The displayed segmented model can be displayed using a surface representation, a wireframe representation, a representation comprising discrete elements, or any combination thereof. During the registration process, once an initial registration is determined, the segmented model can be displayed on visor 400 at the expected location thereof, as determined by the registration of the 3D dataset in the reference coordinate system. The segmented model may be presented in a space stabilized manner providing an augmented reality scene to the user. As the registration progresses, the displayed segmented model and the object become better aligned, providing the user with a visual indication regarding registration errors and the progress of registration. The error may be visually estimated from a relative location of markers and corresponding marker representations (e.g., the location of a fiducial marker relative to the representation of the fiducial marker in the segmented model, or the location of the corner of the eye of the patient relative to the location of the corner of the eye in the segmented model). The user may switch the displayed segmented model on or off. For example, the user may switch on the displayed segmented model to provide verification and then switch off the displayed segmented model to prevent distraction. As a further example, the displayed segmented model can be switched on in a display mode where the segmented model fades in and out of view on the display, thus providing a view of both the region of interest (i.e., "the real world") and the segmented model.

According to a further embodiment, some or all of the markers may be located in the 3D dataset by designating these markers on a segmented model using a portable unit instead of employing the above mentioned touchscreen or a mouse and a standard monitor for manual localization of markers in the 3D dataset. The coordinate system of the segmented model is the same as the coordinate system of the model (e.g. the 3D dataset). Following is an example relating to identifying and designating markers for registering a model coordinate system with a reference coordinate system, employing a tracked portable unit which includes a display and an optical detection assembly and specifically by designating the markers with using the portable unit. In the explanation which follows the portable unit is exemplified as an HMD. However, the portable unit may also be, for example, a tablet computer. In the example where the portable unit is a tablet, the tablet is tracked and the user views, via the tablet screen, an image of the patient that is acquired by a camera facing the patient on the rear side of the tablet. In this case, registration related information and augmented reality overlays are presented by overlaying on this image.

Reference is now made to FIGS. 7A-7E, which are schematic illustrations of an exemplary process, where marker representations (e.g., representations of fiducials, representation of anatomical elements) are designated on a segmented model 470 of an object with a designation symbol 466 located on a visor 450 of an HMD during registration, in accordance with a further embodiment. Herein, the verb to designate and designation relates to employing a portable unit (e.g., HMD) for aligning a designation symbol (e.g., designation symbol 466) with a specific point respective of a marker or a marker representation, and to instructing the processor (e.g., by pressing a foot switch or any other user interface device) to determine position related information (in the case of a marker) or location information (in the case of a marker representation) based on the P&O of the portable unit and the display location of the designation symbol at the time of designation. In some cases the processor proceeds and determines the position related information or the location information without direct instructions. For example, when the processor identifies that the HMD is stationary during the designation for a predetermined period of time (e.g., 0.5 seconds). In such a case the processor samples the P&O of the HMD P&O after that predetermined period of time and determines the position related information or the location information.

Figure 7A:
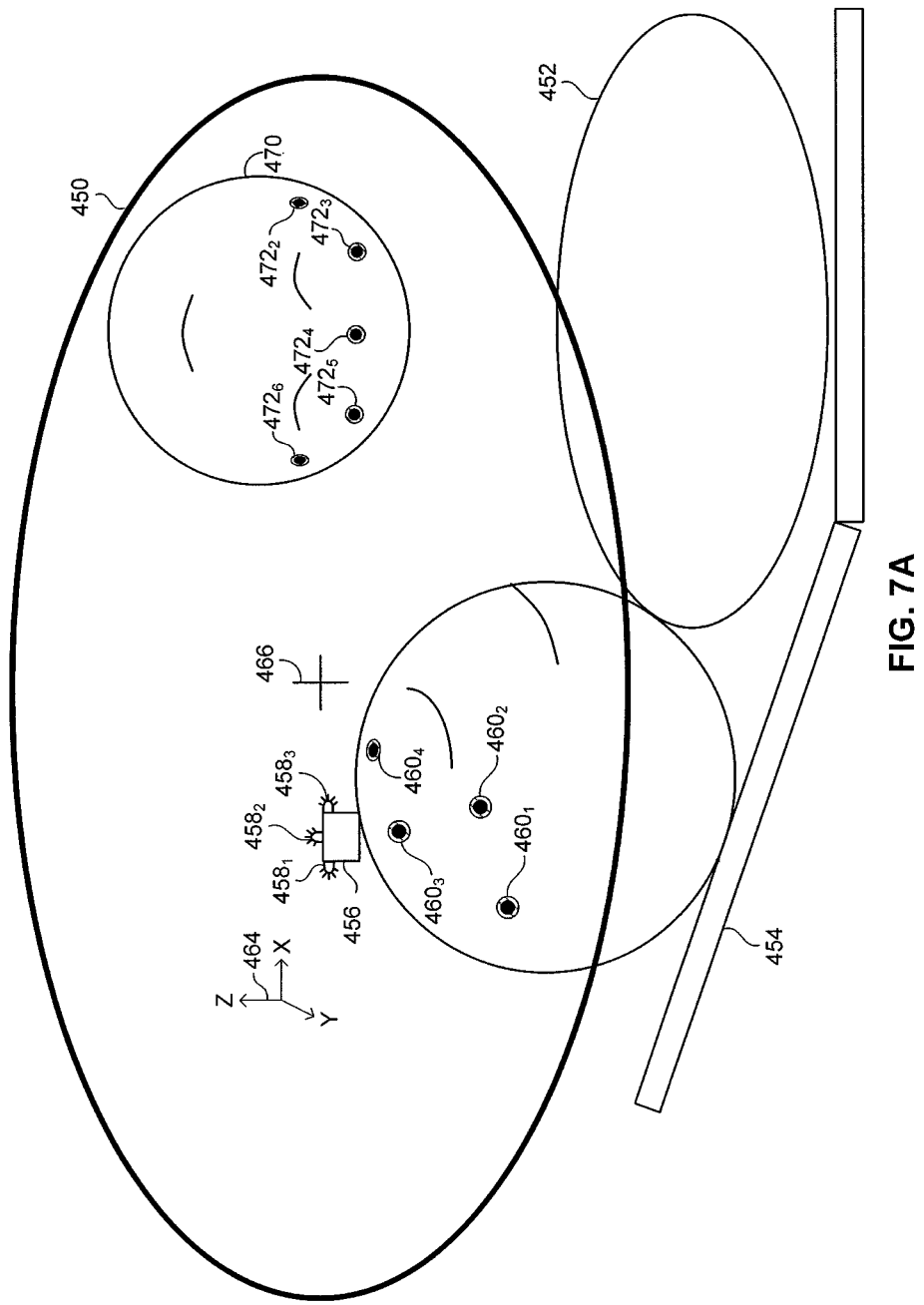
FIGS. 7A-7E are schematic illustrations of an exemplary process, where marker representations are designated on a segmented model of an object with a designation symbol located on a visor of an HMD during registration, in accordance with a further embodiment.

Segmented model 470 is associated with a selected P&O in reference coordinate system 464, and displayed in a space stabilized manner via the HMD, as illustrated in FIG. 7A. The term 'associated with a selected P&O' relates herein to associating the origin of the coordinate system of the model with a selected P&O in the reference coordinate system. An image of segmented model 470 is rendered on visor 450 based on this selected P&O of segmented model 470 and the P&O of the HMD. For instance, initially the selected position of segmented model 470 can be above the general location of patient 452, as determined from the location of tracker reference unit 456, and the selected orientation of model 470 can be arbitrary. Segmented model 470 is displayed such that when the user lifts their head from patient 452, segmented model 470 is visible to the user. The user may then move and/or rotate segmented model 470.

Figure 7B:
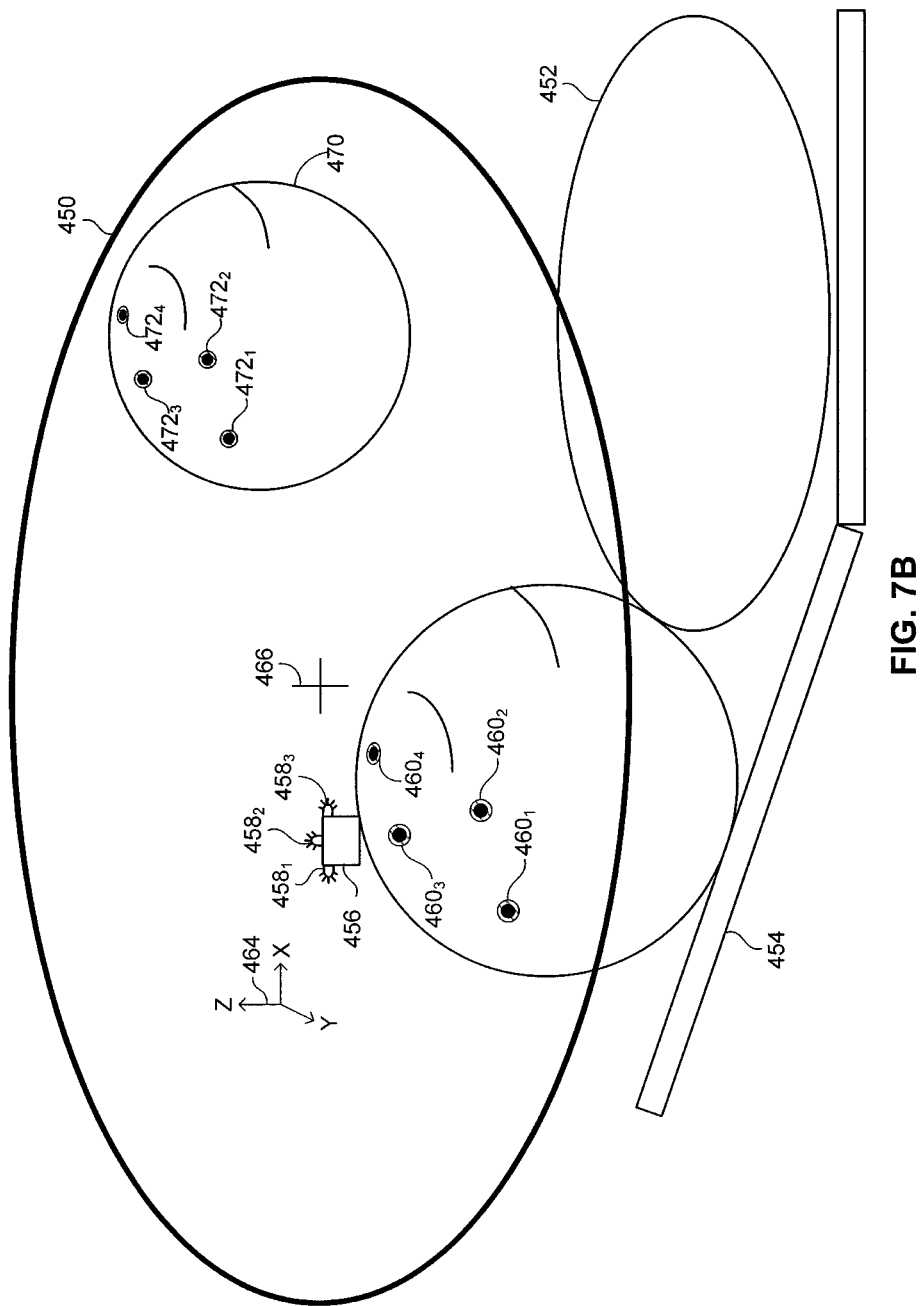
Figure 7C:
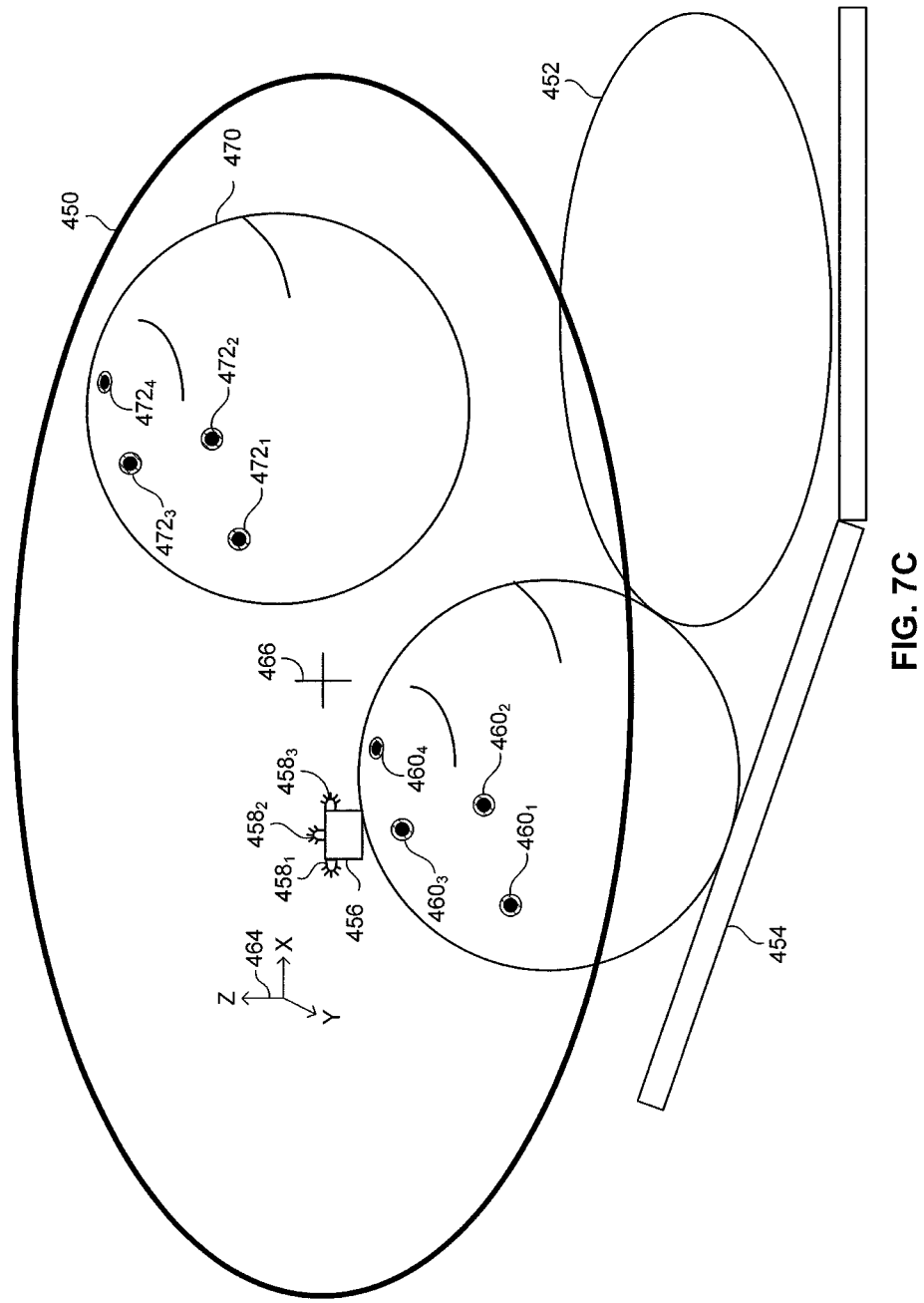

With reference to FIGS. 7B and 7C, after model 470 is positioned at a selected P&O in reference coordinate system 464, the user may rotate segmented model 470 to a new orientation and enlarge or reduce the size of the displayed model (i.e., zoom in or zoom out of displayed segmented model 470) employing a user interface (e.g., using a foot switch, head gestures, and/or voice commands). In general, the user may rotate segmented model 470 such that the marker representations to be designated are generally presented orthogonally to the Line Of Sight (LOS) of the user, thus allowing the user to position the designation symbol over the marker representation to be designated as accurately as possible. Alternatively or additionally, the user may rotate segmented model 470 such that it is generally in the same orientation as the corresponding part of the patient (e.g. the patient's head in FIGS. 7A-7E), such that the user can designate locations of a marker both on the segmented model and the patient from the same registration position, as described further below.

Figure 7D:
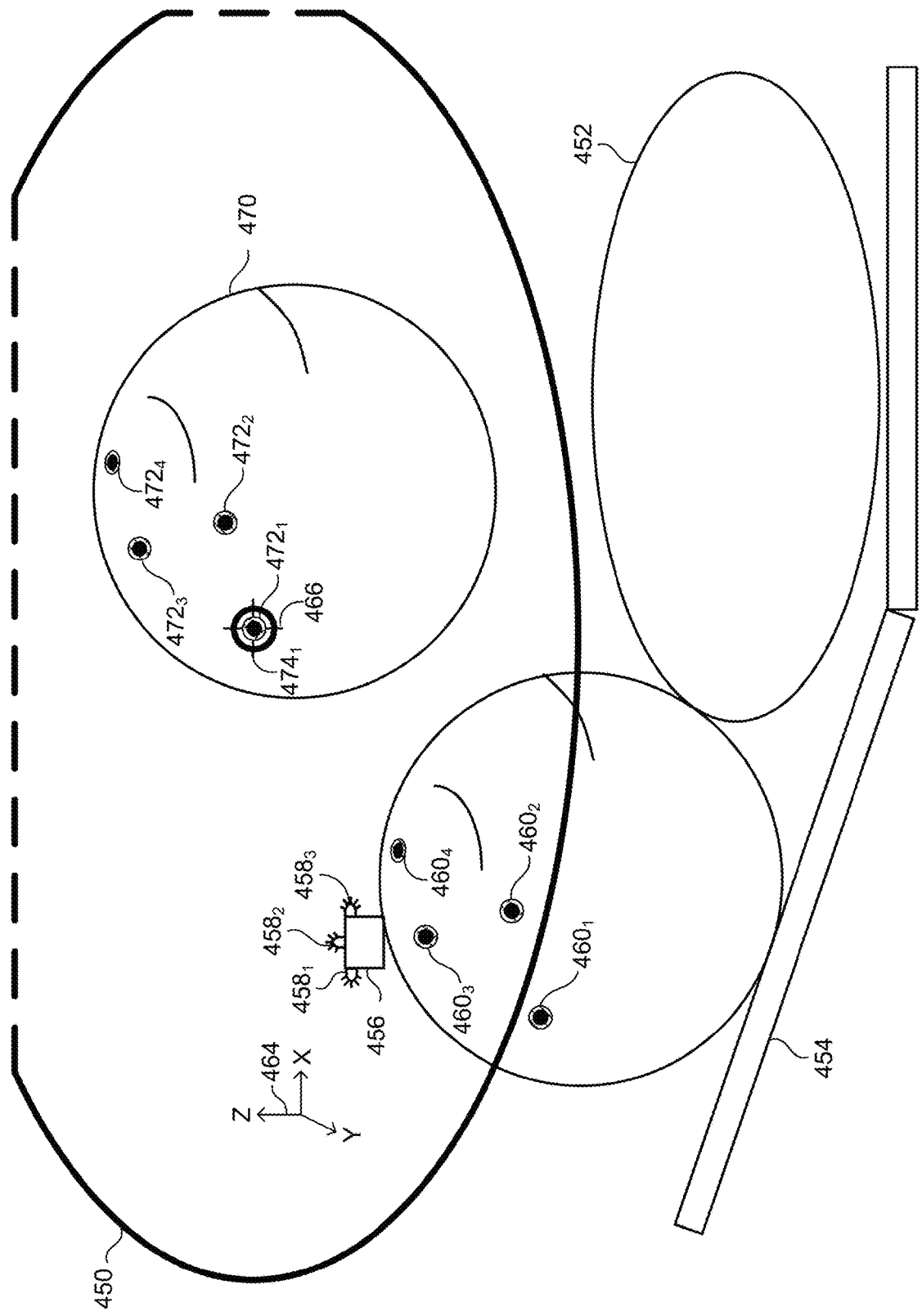

With reference to FIG. 7D, the user positions designation symbol 466 over marker representation $472_1$, such that designation symbol 466 is visually aligned with marker representation $472_1$. The user positions designation symbol 466, for example, by moving her head. The designation symbol 466 is in a fixed location in the display so by rotating her head, the user can align the designation symbol with a point in the segmented model that is visible on the display (e.g. the segmented model is displayed in a space-stabilized manner, so it appears as staying in the same location in space when the user rotates her head). Alternatively, the user aligns designation symbol 466 with marker representation $472_1$ by moving designation symbol 466 in the display (e.g., using a user interface such as pressing a footswitch button to enable control over the location of designation symbol 466 in the display, for instance by rotating the head). The P&O of the HMD in the reference coordinate system and the display location of the designation symbol 466 define a direction (e.g. a vector or a line) in space. When designation symbol 466 is aligned with marker representation $472_1$ this line intersects segmented model 470 at the location respective of marker representation $472_1$ in the reference coordinate system. The location of marker representation $472_1$ can be determined from the intersection of segmented model 470 with the line defined by the P&O of the HMD. The user employs a user interface (e.g., a foot switch, voice command, or blinking of the eye when the HMD includes an eye tracker) to designated marker representation $472_1$, e.g. to instruct the processor to sample the designated location. Once the marker representation $472_1$ is associated with a location in the reference coordinate system 464, the location of marker representation $472_1$ in the model coordinate system (e.g. which is also the coordinate system of segmented model 470) can be determined (e.g. based on the P&O of the segmented model 470 in the reference coordinate system). Furthermore, a marker indicator $474_1$ is rendered on the image displayed on visor 450 such that marker indicator $474_1$ is aligned with marker representation $472_1$.

Figure 7E:
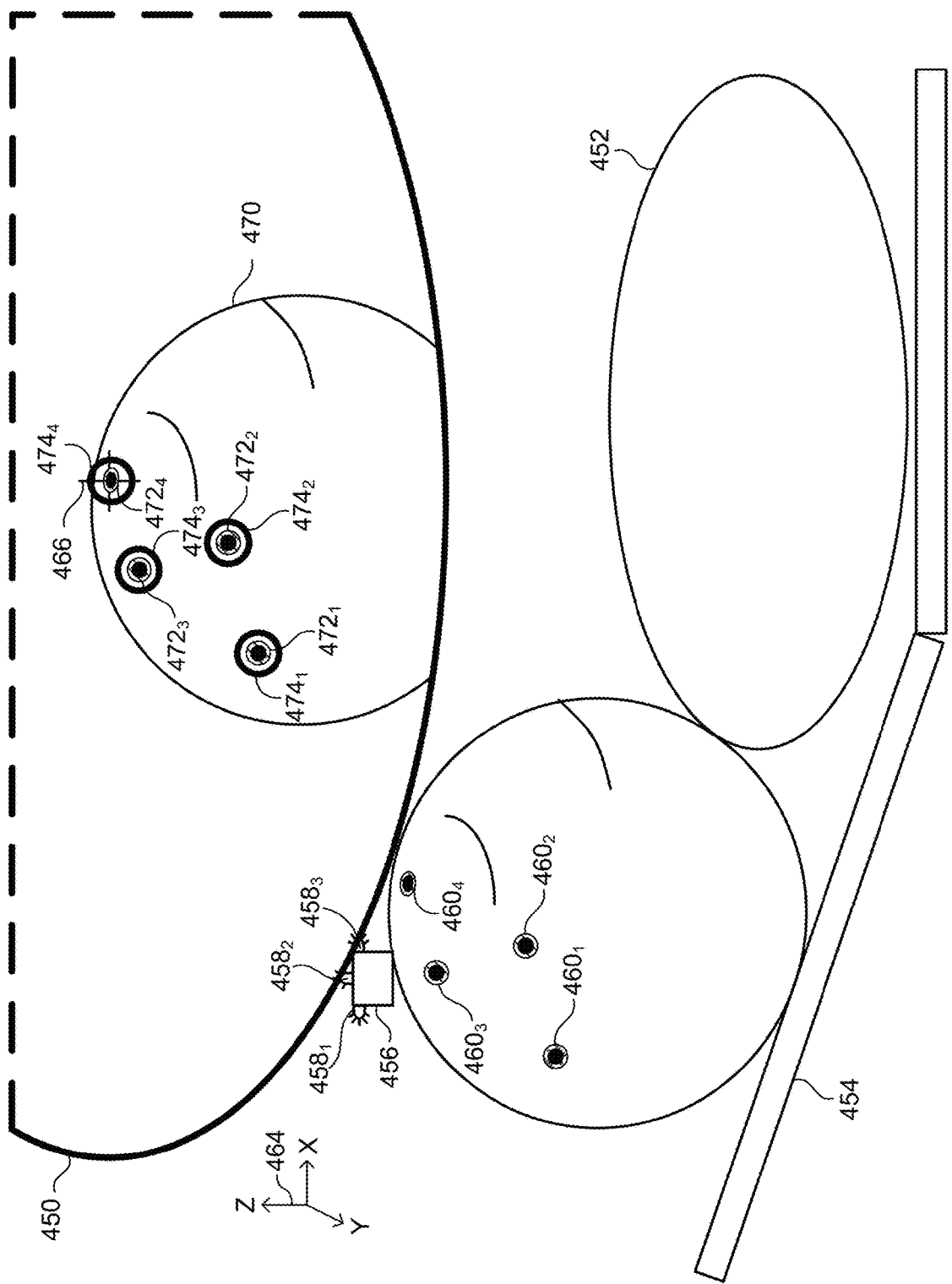

Similarly, and with reference to FIG. 7E, the user designates each one of marker representations $472_2$-$472_4$. Consequently, the location of each one of marker representations $472_2$-$472_4$ in the model coordinate system is also determined (i.e., as described above for marker representation $472_1$). Marker indicators $474_2$-$474_4$ are rendered on the image displayed on visor 450 such that each marker indicator $474_2$-$474_4$ is aligned with a respective marker representation $472_2$-$472_4$. The user may continue and rotate segmented model 470 to designate additional marker representations that are not visible in the current orientation.

With reference to FIGS. 7A-7E, the user can position segmented model 470 in an orientation similar to the orientation of patient 452. Thus, when the user moves around patient 452, the user can simultaneously see all corresponding markers both on segmented model 470 and on patient 452, and does not need to rotate segmented model 470. Also, FIGS. 7A-7E describe designation of marker representations from a single direction. It should be noted that marker representations $472_1$-$472_4$ may be designated from multiple directions to improve accuracy of the determined location (e.g. by averaging over the locations determined from the various designations). Furthermore, segmented model 470 hereinabove is brought forth as an example. In general, any information derived from the 3D dataset may be presented to the user to aid in the designation of the marker representations. This information may be for instance raw slice images, oblique slice images, layered models in which the user may choose which layer to present. For example, once the user designates a marker representation, the processor (e.g., in accordance with a user selection) displays a window, Picture-In-Picture or a side-screen showing slices centered on the marked area. The user can scroll between slices, zoom in or out, and refine the designated location. The designation method described in FIGS. 7A-7E and FIGS. 8A-8H was exemplified using artificial markers. However, the same method may be applied to anatomical markers as well.

Before, after or in conjunction with designating marker representations on segmented model 470, the user similarly designates markers located on the patient. Reference is now made to FIGS. 8A-8H, which are schematic illustrations of an exemplary designation process where markers (e.g., fiducials) are designated with a designation symbol 496 located on a visor 480 of a HMD, in accordance with another embodiment. The user observes patient 482 lying on surgical table 482. In the example set forth in FIGS. 8A-8H, a reference unit 486 is at a fixed position and orientation relative to the head of patient 482. Reference unit 486 may be any one of the reference units described above. In the example brought forth in FIGS. 8A-8I, reference unit 486 includes three LEDs $488_1$, $488_2$ and $488_3$. Alternatively, reference unit may include magnetic field transmitters or receivers as explained above. Furthermore, markers are associated with patient 482 (i.e., either fiducials or anatomical landmarks or both). In FIGS. 8A-8H, markers $490_1$, $490_2$, $490_3$, $490_4$, $490_5$, $490_6$ and $490_7$ are depicted. In FIGS. 8A-8H, a user observes patient 482 through a transparent visor. The visor is a part of an HMD (e.g., HMD 218 in FIG. 2). A designation symbol 496 is projected on the visor (e.g. displayed via the HMD). In FIGS. 8A-8H the designation symbol is depicted as a cross. However, the designation symbol may exhibit any shape, for example, the shape of a circle, a square, a star or a dot. It is noted that regardless of the order in which the user designates markers and marker representations, the user may choose to display a segmented model (e.g., model 470 and the marker representations $472_1$-$472_4$) on visor 480 while designating markers $490_1$-$490_7$, so the user can simultaneously see the designated markers and corresponding marker representations (not shown in FIGS. 8A-8H for clarity purposes).

Figure 8A:
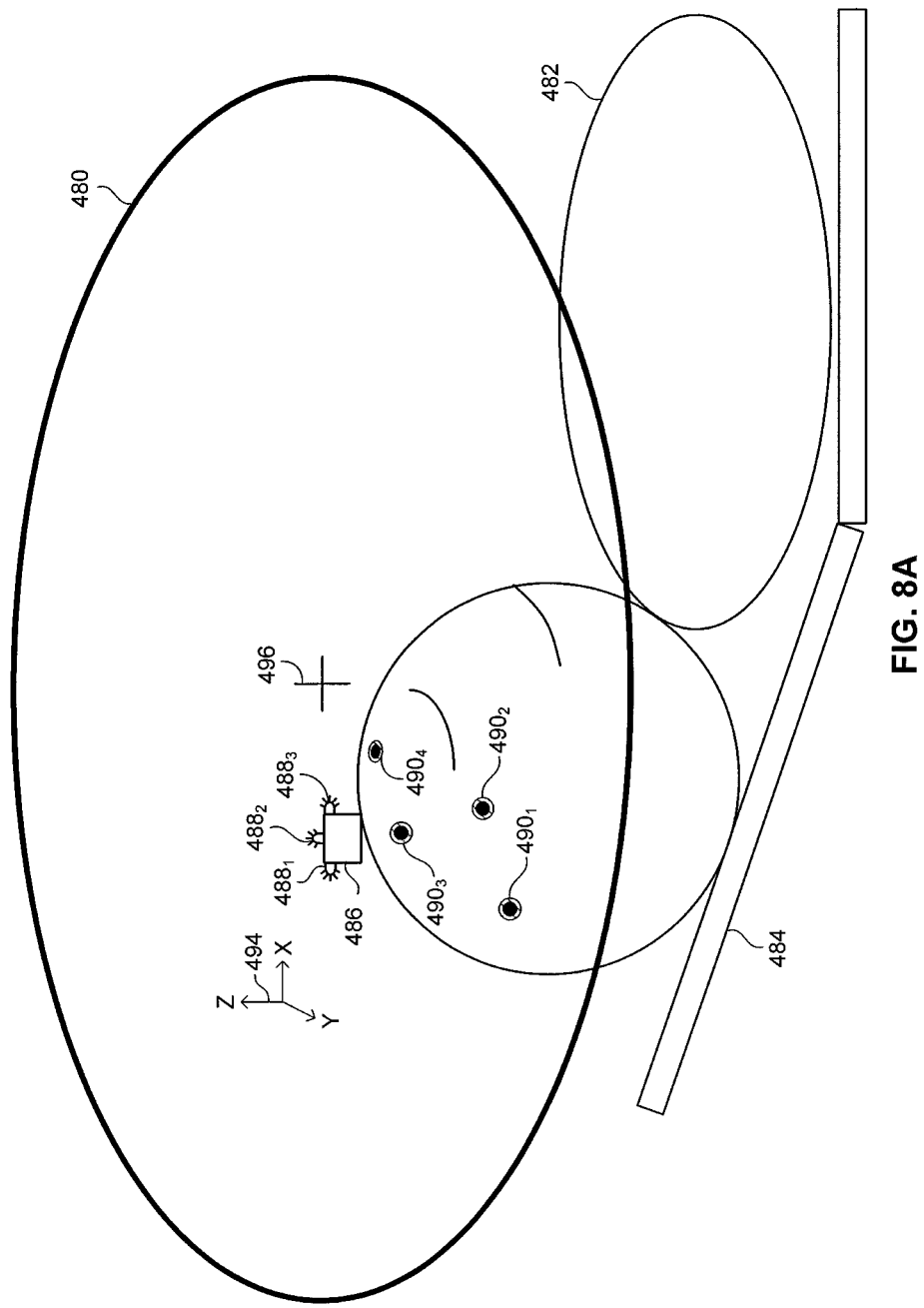
Figure 8C:
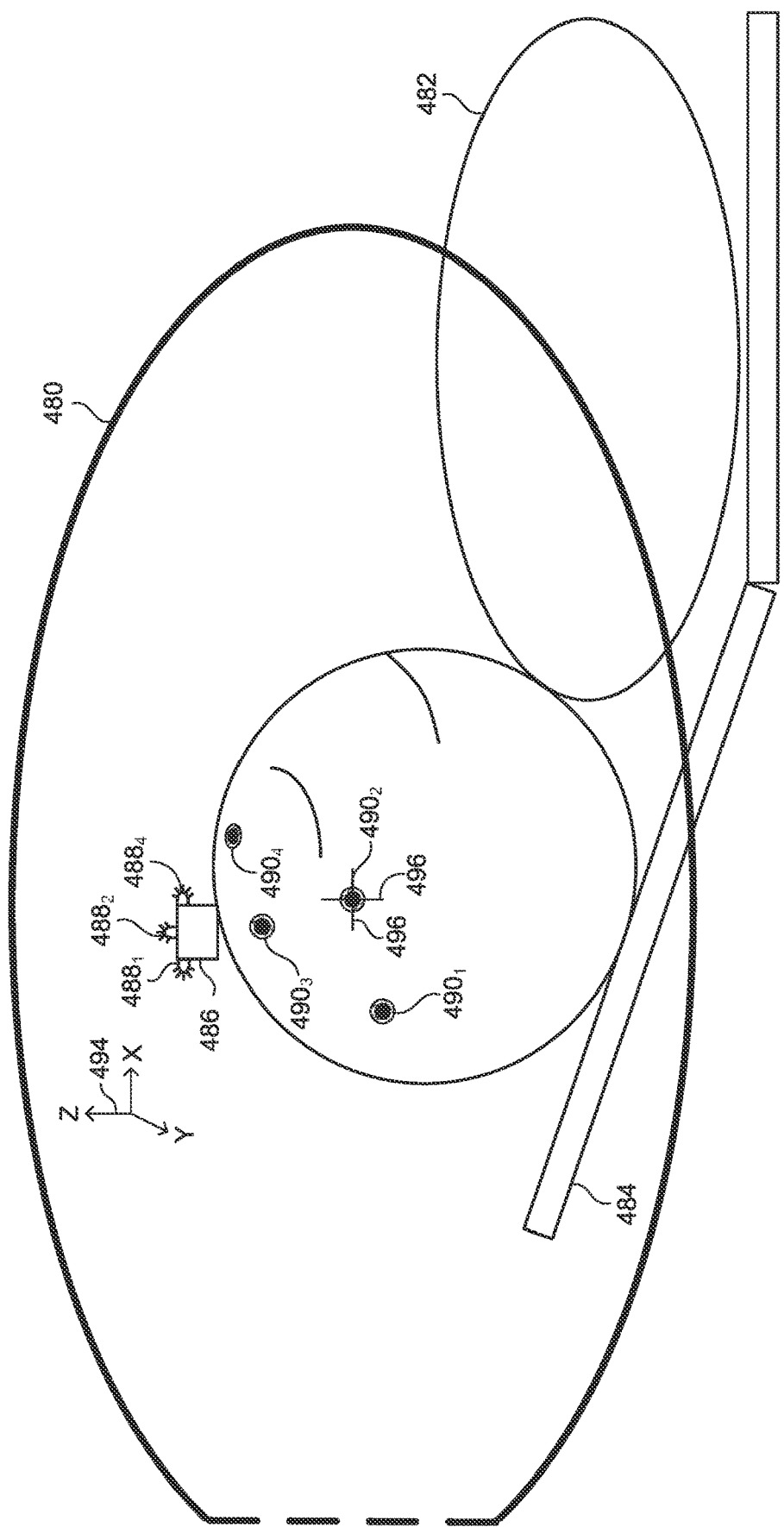
Figure 8D:
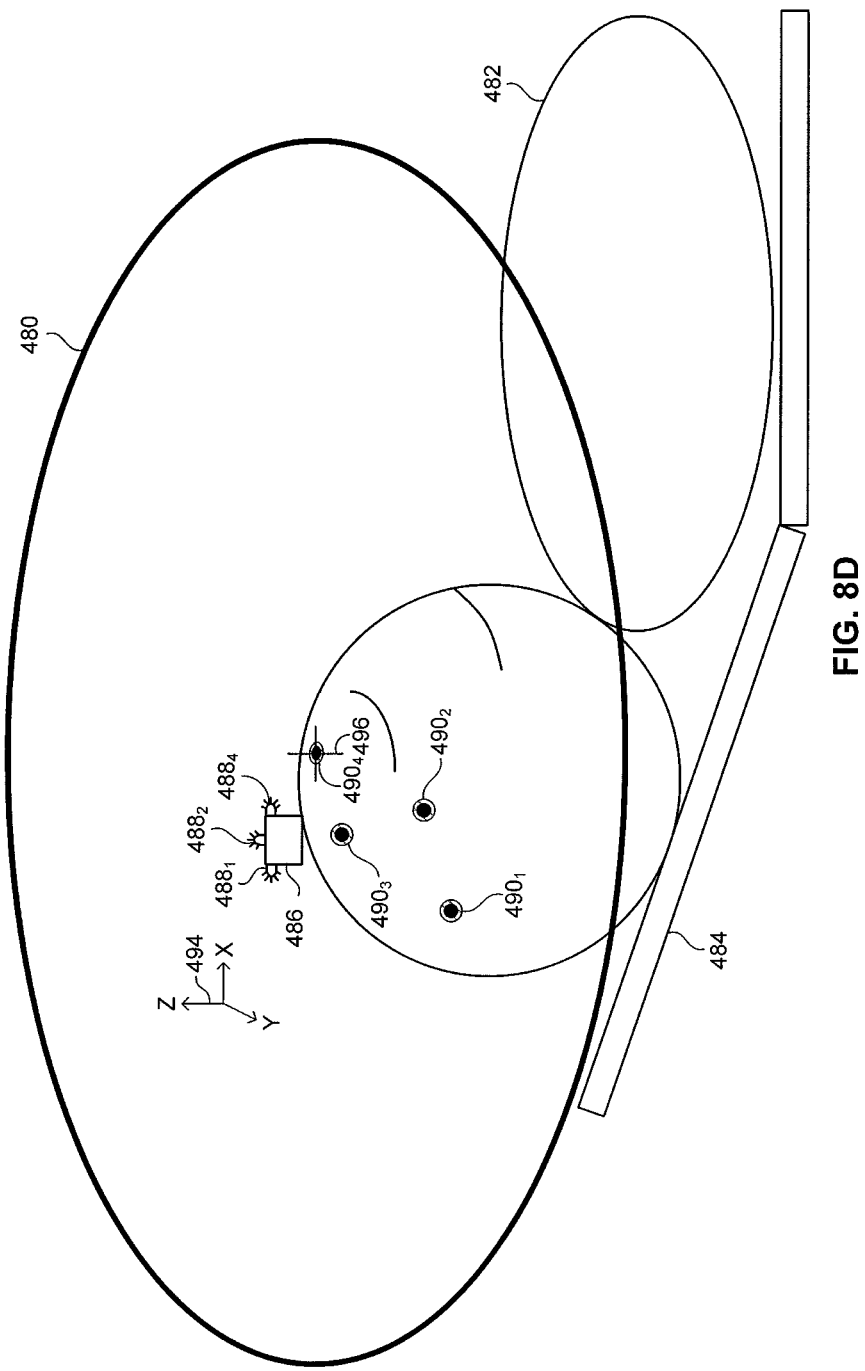

With reference to FIG. 8B-8D, the user is located at a first registration position. With reference to FIG. 8B, the user designates marker $490_1$ with designation symbol 496 by positioning designation symbol 496 over marker $490_1$, such that designation symbol 496 is visually aligned with marker $490_1$. For example, the user positions designation symbol 496 over marker $490_1$ by moving her head or by moving designation symbol 496, and then presses a switch (e.g., a foot switch, a switch of a hand-held remote control). With reference to FIG. 8C-8D, the user moves her head such that designation symbol 496 is visually aligned with marker $490_2$, $490_3$ and marker $490_4$, and the user designates these markers.

Figure 8E:
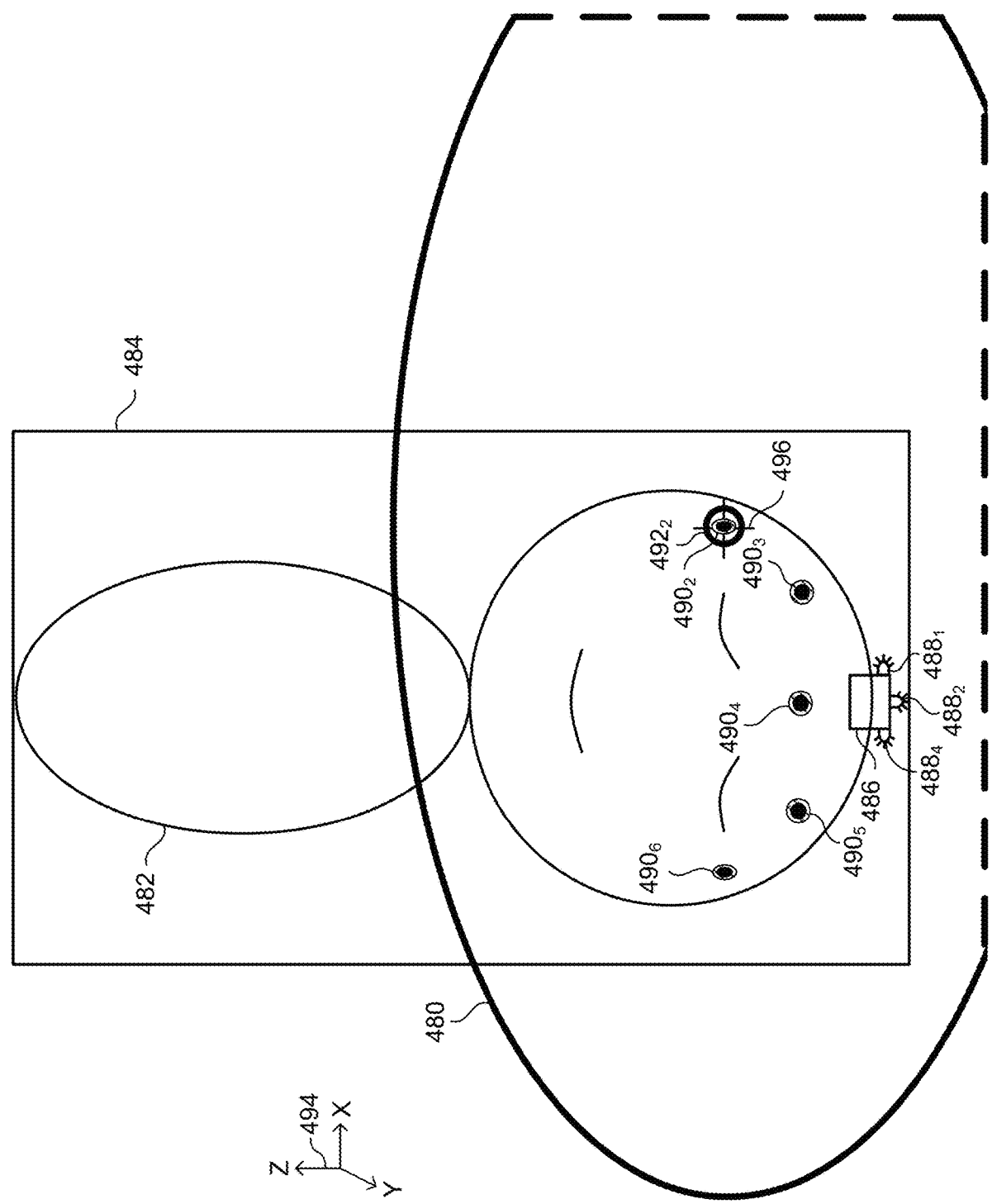
Figure 8F:
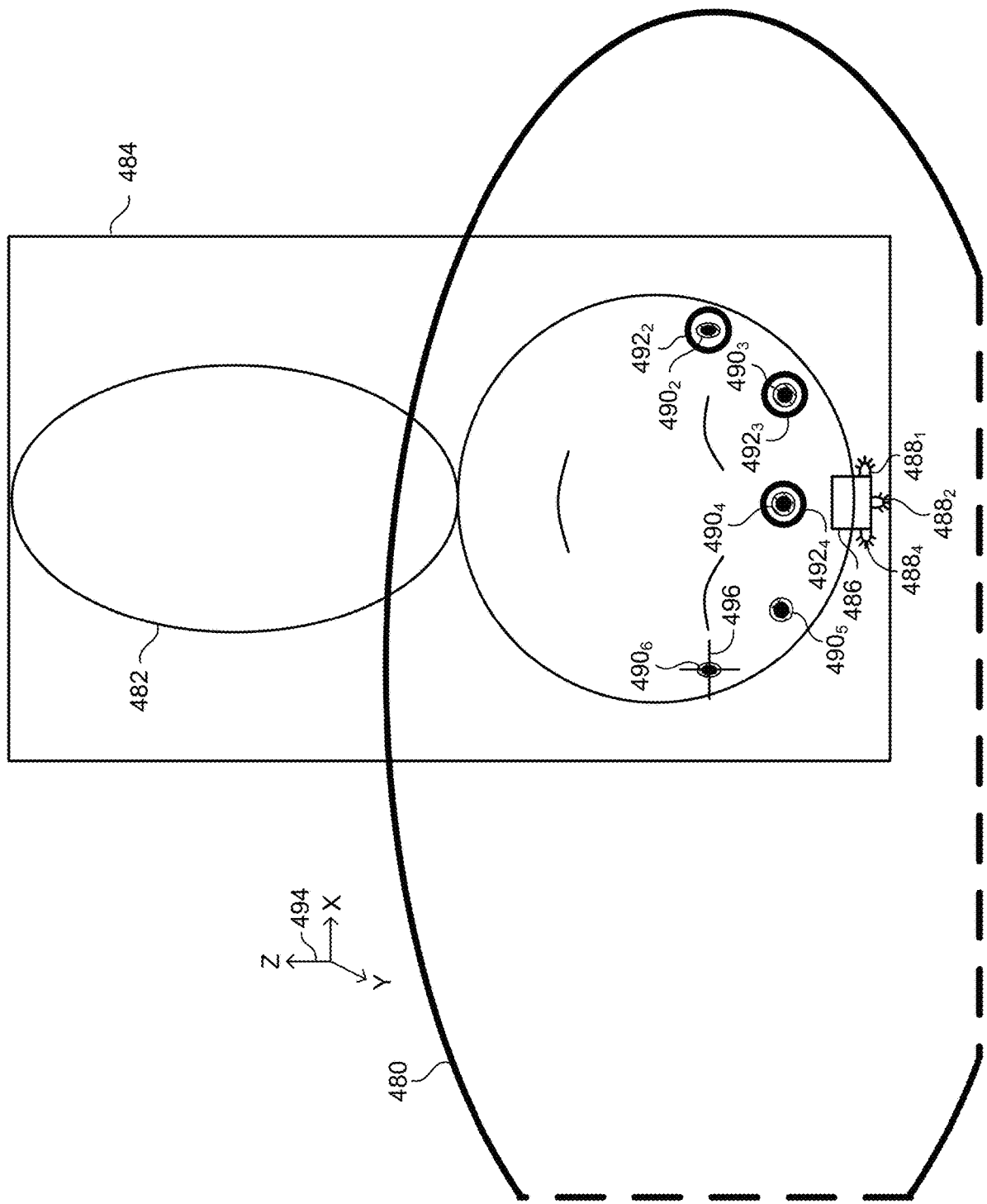

With Reference to FIGS. 8E and 8F, the user is located at a second registration position. With reference to FIG. 8E, the user designates marker $490_2$ by moving her head, and positioning designation symbol 496 over marker 490$_2$, such that designation symbol 496 is visually aligned with marker 490$_2$. Thus, marker 490$_2$ is designated from two different viewing positions, and the position of marker 490$_2$ can be determined. Consequently, marker 490$_2$ is designated by a respective marker indicator 492$_2$. Similarly, with reference to FIG. 8F, the user designates markers 490$_3$ and 490$_4$. Thus, markers 490$_3$ and 490$_4$ are designated from two different viewing positions, and the position of markers 490$_3$ and 490$_4$ can be determined, and markers 490$_3$ and 490$_4$ are designated by respective marker indicators 492$_3$ and 492$_4$.

Figure 8G:
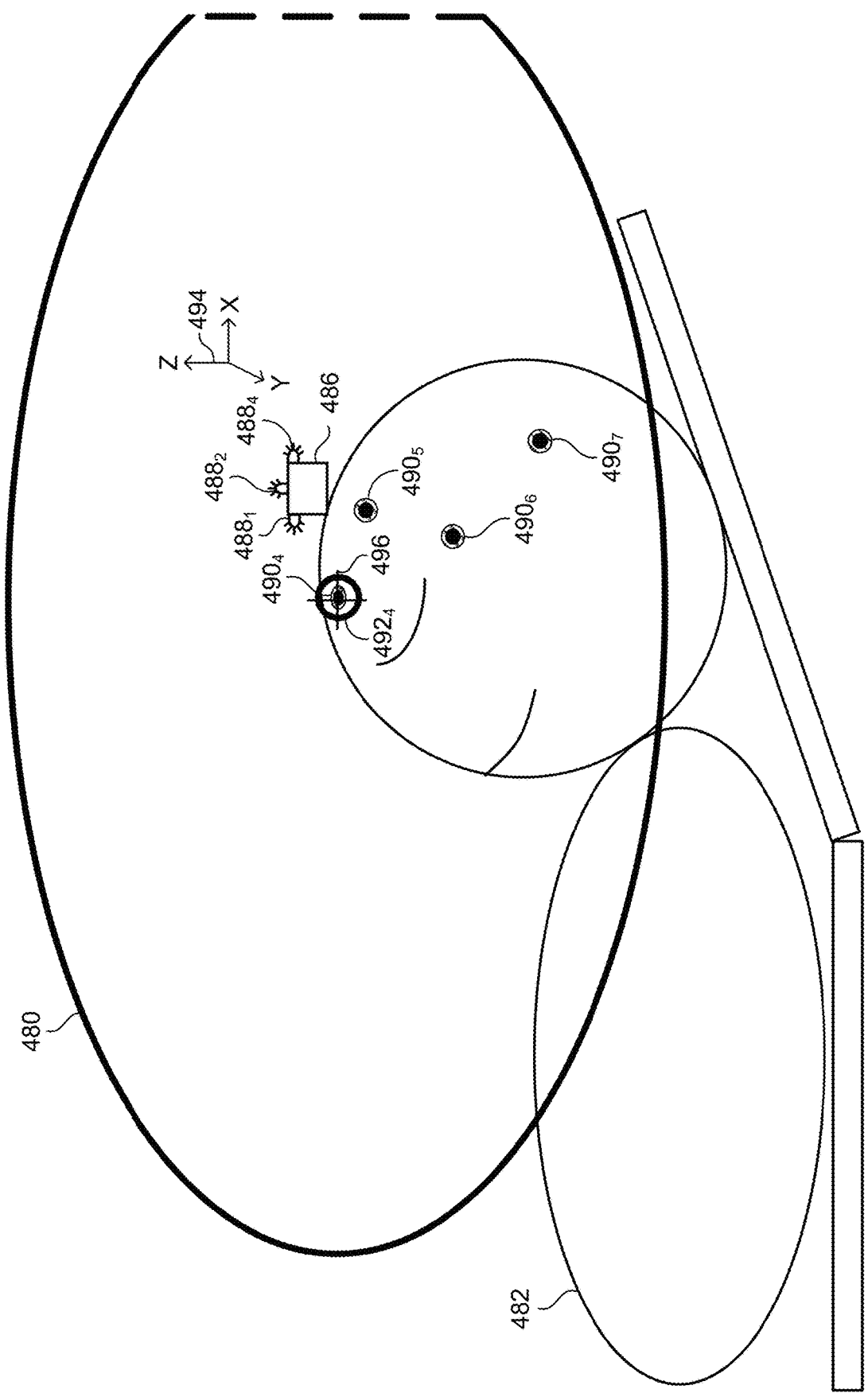
Figure 8H:
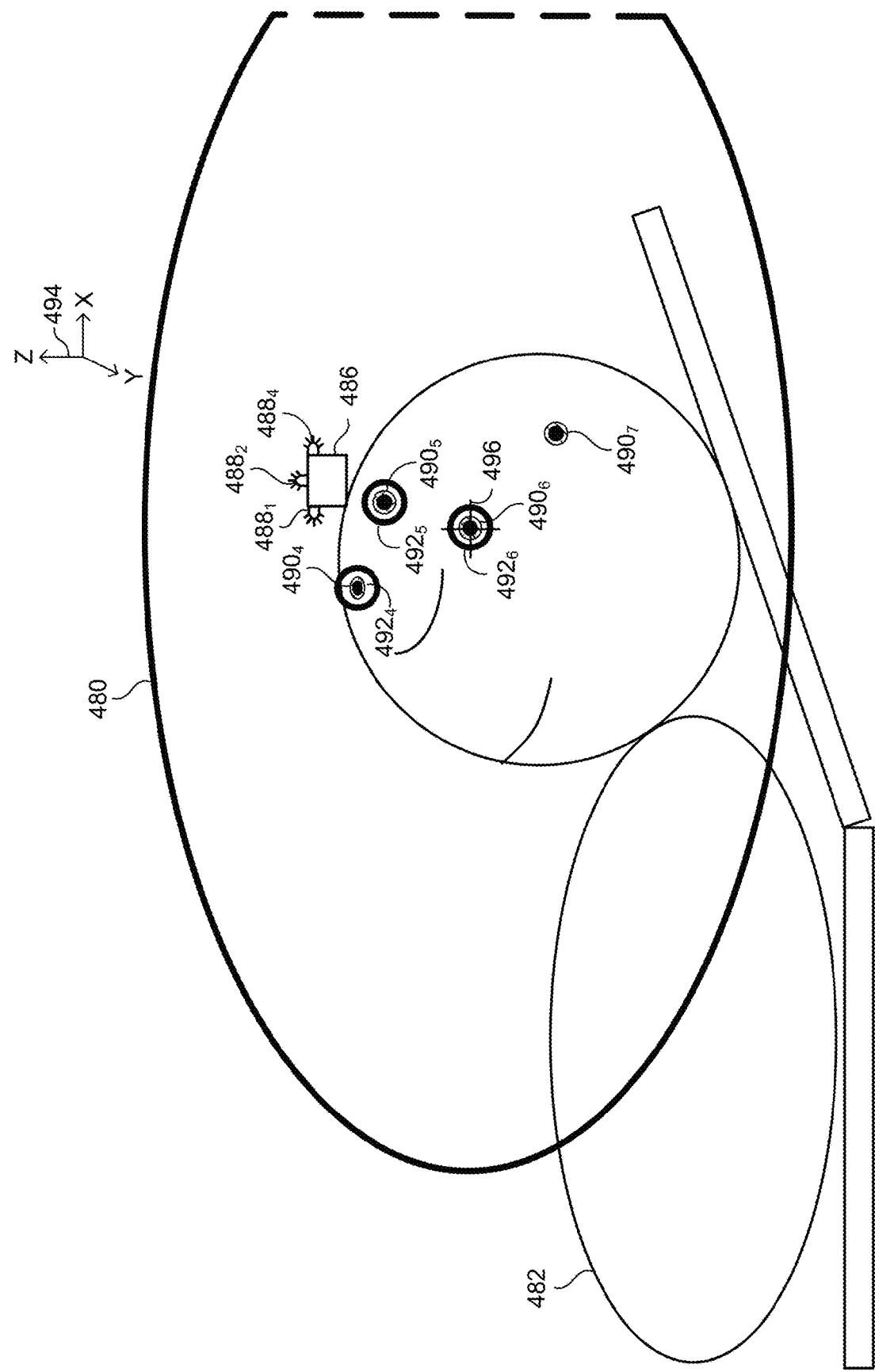

With Reference to FIGS. 8G and 8H, the user is located at a third registration position. With reference to FIG. 8G, the user designates marker 490$_4$ by moving her head, and positioning designation symbol 496 over marker 490$_4$, such that designation symbol 466 and marker 490$_4$ are visually aligned. Thus, marker 490$_4$ is designated from three different viewing positions. Similarly, with reference to FIG. 8H, the user designates markers 490$_5$ and 490$_5$. Thus, markers 490$_5$ and 490$_6$ are designated from two different viewing positions, and the position of markers 490$_5$ and 490$_6$ can be determined, and markers 490$_5$ and 490$_6$ are designated by respective marker indicators 492$_5$ and 492$_6$. In FIG. 8H, the user opts not to designate marker 490$_7$.

With reference to FIGS. 7A-7E and 8A-8G, each one of markers 490$_1$, 490$_2$, 490$_3$, 490$_4$, 490$_5$ and 490$_6$ is associated with a corresponding marker representations 472$_1$, 472$_2$, 472$_3$, 472$_4$, 472$_5$ and 472$_6$, for example, based on tags. According to one exemplary alternative, when the user designated marker representations 472$_1$, 472$_2$, 472$_3$, 472$_4$, 472$_5$ and 472$_6$ on segmented model 470, these marker representations are automatically tagged (e.g., "tag 1", "tag 2", "tag 4", "tag 5" and "tag 6"). Thereafter, a user chooses one of the tags (e.g., "tag 1") and designates a corresponding marker (e.g., marker 490$_1$) on the patient. The user repeats this for selected tags. Alternatively, the user designated markers 490$_1$, 490$_2$, 490$_3$, 490$_4$, 490$_5$ and 490$_6$ on patient 452 and these markers are automatically tagged (e.g., "tag 1", "tag 2", "tag 4", "tag 5" and "tag 6"). Thereafter, the user chooses one of the tags (e.g., "tag 1") and designates a corresponding marker representation (e.g., marker 472$_1$) on the segmented model 470 and repeats for all selected tags. Tagging can be avoided by designating a marker representation on the segmented model (e.g., marker representation 472$_1$) and immediately designating a corresponding marker (e.g., marker 490$_1$) on patient, or vice versa. Tagging may further be avoided if a one to one correspondence is automatically identified by the registration algorithm between markers and marker representations (e.g., according to the spatial relationships between the markers and the spatial relationships between the marker representations). In general the association between markers 490$_1$, 490$_2$, 490$_3$, 490$_4$, 490$_5$ and 490$_6$, with a corresponding marker representation 472$_1$, 472$_2$, 472$_3$, 472$_4$, 472$_5$ and 472$_6$ is also applicable when designation is performed automatically or semi-automatically. Automatic and semi-automatic designation is further elaborated below.

In the description above, the marker indicators 412$_1$-412$_6$ (FIGS. 6A-6D), marker indicators 474$_1$-474$_6$ (FIGS. 7A-7E), and marker indicators 492$_1$-492$_4$ (FIGS. 8A-8H) are presented as circles around the respective marker. However, these marker indicators may be of any form or shape which enables to visually assess the accuracy of the designation (e.g., a dot or ball shape). Further in the description above, a marker is designated from two different directions to determine the location thereof in the reference coordinate system. However, employing the designation method described above in conjunction with FIGS. 8A-8H, it is sufficient to designate a marker from only one direction. The line defined by the designation provides constraints on the location of the marker. Providing a sufficient number of markers are designated (e.g., three markers), along with the locations of the corresponding marker representations in the 3D dataset (e.g. the model), provides sufficient information to register the model with the reference coordinate system.

As mentioned above, the marker representations may be automatically designated or semi-automatically designated. Automatic designation or semi-automatic (i.e., user assisted) designation relates herein to determining, by a processor employing algorithms, position related information associated with markers in the reference coordinate system or 3D locations of marker representations in the model coordinate system.

In the case of markers, automatic designation and semi-automatic designation are based on automatically detecting and localizing (i.e., determining the location) of the markers in acquired images of the patient (e.g. images acquired by the optical detection assembly). In the case of semi-automatic designation, the detection and localization algorithms are limited to process only a designated area in the image (e.g. a region of interest—ROI). In the case of automatic designation the detection and localization algorithms process the entire image and are not limited to process only a designated area in the image. In semi-automatic designation the process is initiated when the user designates an area on the patient using a designation symbol (e.g. a square that designates an area). Upon the user designation an image is acquired by the optical detection assembly. The system (e.g., processor 214—FIG. 2, processor 256—FIG. 3, processor 306—FIG. 4, processor 356—FIG. 5) determines an ROI in the acquired image that corresponds to the designated area (e.g. an ROI in the image that represents the designated area on the patient) and automatically detects the marker in the ROI. The corresponding ROI is determined based on a known alignment between the camera in the optical detection assembly and the HMD display, and based on the location of the designation symbol in the display. In automatic designation the camera can continuously acquire images at a predefined rate and the processor can process these images to automatically detect and localize markers. When employing a tablet computer, user designates areas on the image of patient 452 shown on the tablet computer display.

In the case of marker representations, automatic designation and semi-automatic designation are based on automatically detecting and localizing the markers in the 3D dataset. In the case of semi-automatic designation, the detection and localization algorithms are limited to process only a designated volume in the 3D dataset. In the case of automatic designation the detection and localization algorithms process the entire 3D dataset and are not limited to process only a designated volume. In semi-automatic designation the process is initiated when the user designates an area on the segmented model using a designation symbol (e.g. a square that designates an area). The processor associates a volume within the 3D dataset that corresponds to the designated area and automatically detects the marker representation in that volume. In automatic designation the detection and localization can be performed at any time prior to the surgery or once the surgery begins, as long as the automatic designation is completed prior to the registration.

As described hereinabove, deep learning methods (e.g., trained neural networks) may be employed for the identification and localization (i.e., determining the location) of marker representations in the 3D dataset. Similar to as described above, deep learning methods may be employed to localize markers in representations of said markers acquired by a portable unit. As such, for example, neural networks can be trained to identify markers in images of the patient. For example, a neural network can be trained to identify (e.g. segment) a fiducial having a specific 3D shape, a pen mark on the patient representing a fiducial location (e.g. contour of a circle with dot in the center or other pen marks that corresponds to other types of fiducials), ears, nose or eyes. The same neural network, or another one, can be trained to determine a location respective of the marker in the image. For example, once an eye segment is identified in the image, the network can be trained to determine the location of corner of the eye. The processor uses this location to determine position related information respective of the marker in the reference coordinates system.

Both in automatic and semi-automatic designation, either for designating a marker representation in the 3D dataset or for designating a marker on the patient, the system can present a determined location by providing a marker indicator for the identified marker or marker representation (e.g., a circle, a dot, a small sphere), and the user can approve or correct the designation (e.g., by moving the marker indicator), and select new areas for designation. When presenting the determined location for a marker representation in the 3D dataset, the indicator can be presented on the segmented model and/or on slices from the 3D dataset. During automatic designation of markers on the patient, the processor can instruct the user to move around the patient and/or notify the user regarding the status of the gathered information until sufficient information is acquired and registration can be determined.

Discussed above (e.g., FIGS. 1 and 6A-6D) were special cases of automatic designation, in which the optical detection assembly is implemented with a tracker unit that can detect emitters. In the general case, the optical detection assembly includes a camera and any type of marker can be detected, including artificial markers without dedicated reflectors or LEDs, and anatomical markers.

In general, the user may select to employ any of the designation methods described herein above during the registration procedure. For example, some of the markers may be designated employing a tracked tool while others may be designated employing an HMD and/or automatic or semi-automatic designation. The designation method described above enables a single surgeon to perform registration without the aid of additional personal such as a second surgeon aiding with the designation of marker representations on a touchscreen.

Figure 9:
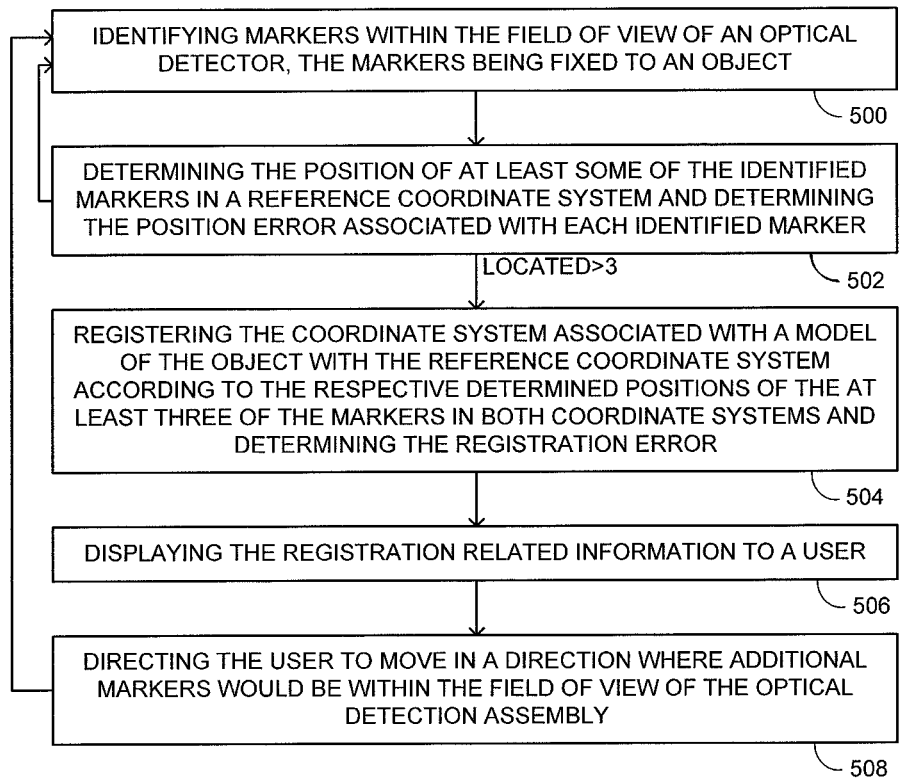
FIG. 9 is a schematic illustration of a method for displaying registration related information to a user, in accordance with a further embodiment.

Reference is now made to FIG. 9, which is a schematic illustration of a method for displaying registration related information to a user, in accordance with a further embodiment. In procedure 500, markers within the field of view of an optical detector are identified. The markers are fixed to an object. These markers may be fiducial markers or anatomical landmarks. With reference to FIGS. 6A-6D, markers $410_1$, $410_2$, $410_3$, $410_4$, $410_5$, $410_6$ and $410_7$, which are within the field of view of an optical detector are identified.

In procedure 502, the positions of at least some of the identified markers, in a reference coordinate system, are determined. Furthermore, the position error of the identified markers is also determined. With reference to FIGS. 6A-6D, a processor (not shown) determines the position of at least some of markers $410_1$, $410_2$, $410_3$, $410_4$, $410_5$, $410_6$ and $410_7$ in reference coordinate system 414. When the positions of at least three markers are identified, the method proceeds to procedure 424. Otherwise, the method returns to procedure 420.

In procedure 504, the coordinate system associated with a model of the object is registered with the reference coordinate system, according to the respective positions of the at least three of the identified markers in both coordinate systems. Furthermore, the registration error is determined. With reference to FIGS. 6A-6D a processor registers reference coordinate system 414 with the coordinate system associated with a model of patient.

In procedure 506, registration related information is determined and displayed to the user. As mentioned above, registration related information may further include user related information such as user selection or user guidance. With reference to FIGS. 6A-6D, registration related information is displayed on visor 400.

In procedure 508, the user is directed to move in a direction where additional markers would be within the field of view of the optical detection assembly. Since at least initial registration is determined, the location of all markers in the reference coordinate system can be estimated. Thus, the location of these markers relative to the location of the portable unit can also be determined. It is noted that directing the user in a direction where additional markers would be within the field of view of the optical detection assembly is optional and may occur when the registration process is yet to be completed (e.g., when the registration error is above a threshold or the user selects to continue the registration process). With reference to FIG. 6B, the user is directed to move to the right in order to identify and located additional markers. After procedure 428 the method returns to procedure 420.

In general, there are three types of error estimations involved in the registration process. The first is the error estimation (herein 'type one error estimation') relates to the error of the position of a single marker in the reference coordinate system. This error results from the residual error of the triangulation process (i.e., lines intersection), the angular difference between the lines and the location error of the portable unit. This error may be relatively large when the marker was partially obscured from some direction, smudged by blood and the like, or when the angular difference between the directions associated with the marker is relatively small. In such a case the user may be instructed to move to another registration position so the marker may be sampled from an additional direction. The error may also be large if the user moved relatively fast while the marker was sampled (i.e., when the direction from the portable unit toward the marker was determined). Such an error may be detected automatically and the user may be instructed, for example, to move slower. The second type of error estimation for each marker (herein 'type two error estimation') relates to the distance between the position of the markers in the registered model coordinate system (i.e. the image coordinate system after the rotation and translation onto the tracker coordinate system according to the calculated registration) and the position of the marker in the reference coordinate system. A specific marker may have been displaced between the time the imaging was performed and the time the registration is performed, but still be accurately located. In such a case, this marker will exhibit a small estimated error of the first type and a large estimated error of the second type and the system may discard it automatically or recommend to the user to discard it manually. Consequently, the registration may be improved. The third type of error estimation (herein 'type three error estimation')

is the figure of merit of the registration calculation, which may be the average of the errors of the second type for all the markers, or any other objective function (i.e., the objective of the registration calculation is to minimize this error). All of the above types of error estimations may be calculated and displayed to the user (e.g., in millimeters).

Figure 10:
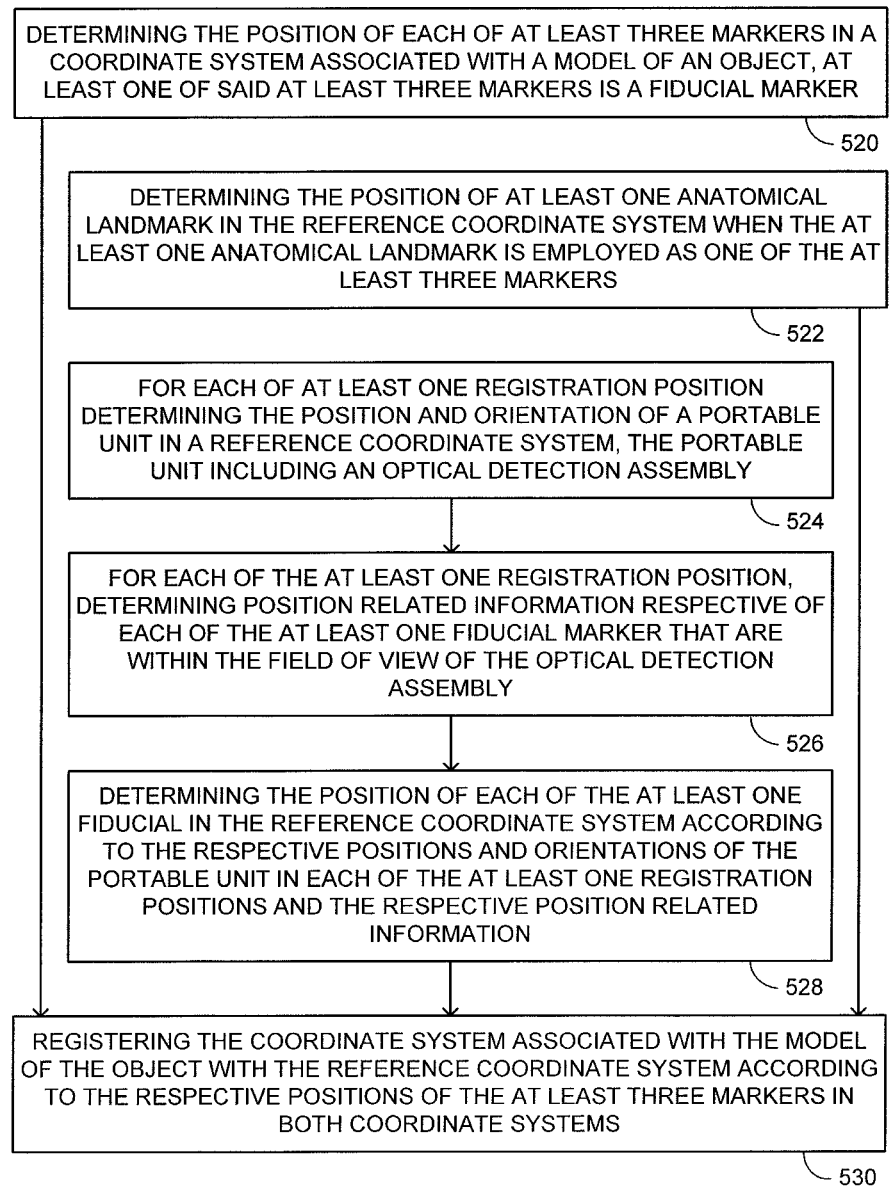
FIG. 10 is a schematic illustration of a method for registering a model coordinate system and a reference coordinate system in accordance with another embodiment of the disclosed technique.

Reference is now made to FIG. 10, which is a schematic illustration of a method for registering a model coordinate system and a reference coordinate system in accordance with another embodiment. In procedure 520, the position of each of the at least three markers is determined in a coordinate system associated with a model of an object. At least one of the at least three markers is a fiducial marker. When the model is, for example, an image, the location of the markers may be determined by employing image processing techniques. Alternatively, the location of markers may be manually marked on a screen. After procedure 520, the method proceeds to procedure 530.

In procedure 522 the position of at least one anatomical landmark is determined in the reference coordinate system, when at least one anatomical landmark is employed as a marker. With reference to FIG. 2, when the at least part of the markers are anatomical landmarks, physician 224 employs a pointer. In such a case medical tool 222 takes the form of a pointer. Physician 224 places the tip of the pointer on the anatomical landmark. Processor 214 determines the location of the pointer (i.e., of medical tool 222), and thus of the marker, in reference coordinate system 230 as described above. After procedure 522, the method proceeds to procedure 530.

In procedure 524, for each of at least one registration position, the position and orientation of a portable unit in a reference coordinate system is determined. The portable unit includes an optical detection assembly. When the optical detection assembly is an optical detector (e.g., a sensor array camera or a PSD) then, the number of registration positions is at least two. When the optical detection assembly is a stereoscopic camera or a TOF camera, the number of registration positions is at least one. With reference to FIGS. 1A-1C, a user 106 moves moving optical detector 102 (i.e., which, as mentioned above, defined the portable unit together with light emitters $104_1$ and $104_2$) through at least two registration positions. Moving optical detector 102 acquires at least one image of light emitter 110 and moving optical detector acquires at least one image of light emitters $104_1$ and $104_2$. A Processor (e.g., processor 214—FIG. 2) determines the position and orientation of the relative position between reference optical detector and a moving optical detector is determined in reference coordinate system 116 according to the representations of light emitters $104_1$, $104_2$, and 110. With reference to 5, optical tracking module 362 may be embodied as either a TOF camera or a stereoscopic camera which acquires which acquires an image or images of light emitters $360_1$ $360_2$ and $360_3$. Processor 356 determines the location of optical tracking unit 362, and consequently of portable unit 352, in reference coordinate system 368.

In procedure 526, for each of the at least one registration position, location related information respective of each of the at least one fiducial that are within the field of view of the optical detection assembly, is determined. When the portable unit includes an optical detector (e.g., a sensor array camera or a PSD), the position related information includes a respective directions toward each of the at least one fiducial marker located on the object. When the portable unit includes, for example, a stereoscopic camera or a TOF camera, the position related information may be related directly to the position of the fiducial in the reference coordinate system (e.g., two directions from the two detectors in the stereoscopic camera or pixel depth information from the TOF camera). With reference to FIGS. 1A-1C, when moving optical detector 102 acquires the image or images of light emitter 110, moving optical detector 102 also acquires and image of markers $114_1$, $114_2$, $114_3$ and $114_4$. For each registration position, the processor determines position related information of markers $114_1$, $114_2$, $114_3$ and $114_4$, relative to moving optical detector 102, according to the image of markers $114_1$, $114_2$, $114_3$ and $114_4$. With reference to FIG. 5, optical racking module 362 With reference to 5, optical tracking module 362 may be embodied as either a TOF camera or a stereoscopic camera, which acquires an image or images of markers $366_1$ $366_2$ and $366_3$. Processor 356 determines the location of markers $366_1$ $366_2$ and $366_3$ determines the location of the fiducial ones of markers $366_1$ $366_2$ and $366_3$ in reference coordinate system 368.

In Procedure 528, the position of each of the at least one fiducial marker located on the object is determined in the reference coordinate system, according to the positions and orientations of the portable unit in each of at least two registration positions and the respective position related information of each of the at least one fiducial marker. For example each direction defines a line in the reference coordinate system. The intersection of the at least two directions associated with each fiducial defines the location of that fiducial in the reference coordinate system. As mentioned above, in practice these lines may not intersect. In such a case, the point exhibiting the minimum distance to each of the lies is determined as the location of the marker. With Reference to FIGS. 1A-1C and 2, a processor (e.g., processor 214—FIG. 2), determines the position of each of the at least three markers (e.g., markers $114_1$, $114_2$, $114_3$ and $114_4$ in FIG. 2 or $232_1$, $232_2$, $233_3$ in FIG. 2) in reference coordinate system (e.g., referenced coordinate system 116 in FIG. 1 or reference coordinate system 230 in FIG. 2).

In procedure 530, the coordinate system associated with the model of the object is registered with the reference coordinate system, according to the respective positions of at least three of the at least three markers, in both coordinate systems. With Reference to 2, processor 214 registers the coordinate system associated with the model of the object with reference coordinate system 230, according to the respective positions of the markers in both coordinate systems.

The description herein above relates to an automatic registration process with an augmented reality environment, where the registration system displays registration related information overlaid on the display, at a display location which corresponds to the position and orientation of the portable unit and the location of the markers in a reference coordinate system. In general, each one of the displays described above may be hand held or head mounted) or part of any portable unit in general (e.g. attached to a moveable arm). For example, a video see-through portable unit includes a tablet computer and a camera. A video see-through portable unit may alternatively include an HMD with a non-transparent near-eye display and a video camera. In a video see-through portable unit the video from the camera is augmented and displayed to the user in the display. When an optical tracking system is employed for tracking a video see-through portable unit, the camera employed for tracking and for the video see-through may be one and the same. An optical see-through portable unit includes, for example, a tablet computer with a transparent display, or a projector and a half-silvered mirror attached to a movable arm. An optical see-through portable unit may alternatively include an HMD with a visor-projected display or a transparent near-eye display.

The descriptions herein above exemplified the registration process with the user moving through at least two different registration positions. However, in practice, when the location of the markers is determined with the aid of the portable unit, the user may move the portable unit without constraints around the patient, while maintaining the patient within the FOV of the optical detector of the portable unit. The optical detector detects the markers during the motion of the portable unit (e.g., acquires an image when an imaging sensor is employed). The tracking system determines the position and orientation of the potable unit each time a marker is detected and determines the location of the markers as described above, both at a relatively high frequency (e.g., on the order tens of times per second).

The registration procedures according to some embodiments, exemplified in FIGS. 1A-1C, 6A-6D, 7A-7I and 8A-8G employ anatomical (e.g., corner of an eye) or artificial point-like markers (e.g., fiducials) identifiable in both a 3D dataset and on the patient. However, as mentioned above, the marker or marker representations may be an anatomical three dimensional surface or surfaces (e.g., face, bone, torso, limb, head, or e.g. cortex). To register a coordinate system associated with a model with a reference coordinate system, employing a selected surface, a surface representation in the reference coordinate system need to be acquired. Similar to as described above, this surface representation is acquired, for example, by employing a tracked TOF camera, a tracked structured light scanner, a tracked stereoscopic camera or a laser scanner which provides 3D information, or any other 3D surface acquisition techniques. Alternatively to acquiring a surface by the optical assembly, the surface can also be acquired by employing a tracked tool. The tool tip is positioned at a plurality of points on the surface (e.g. moved along the surface) and the location of each of these points in the reference coordinate system is determined, thus generating an ensemble of points representing the surface.

The surface representation in the reference coordinate system is matched with a corresponding surface in the 3D model for example by employing the "head and hat" method. Accordingly, a series of transformations which include homologous point matching is performed. In homologous point matching, each point in the hat (the surface representation) is associated with its nearest head point (3D model). A cost is determined for each transformation. The transformation with the lowest cost is determined as the transformation (i.e., the registration) between the surface representation and the 3D model.

Figure 11:
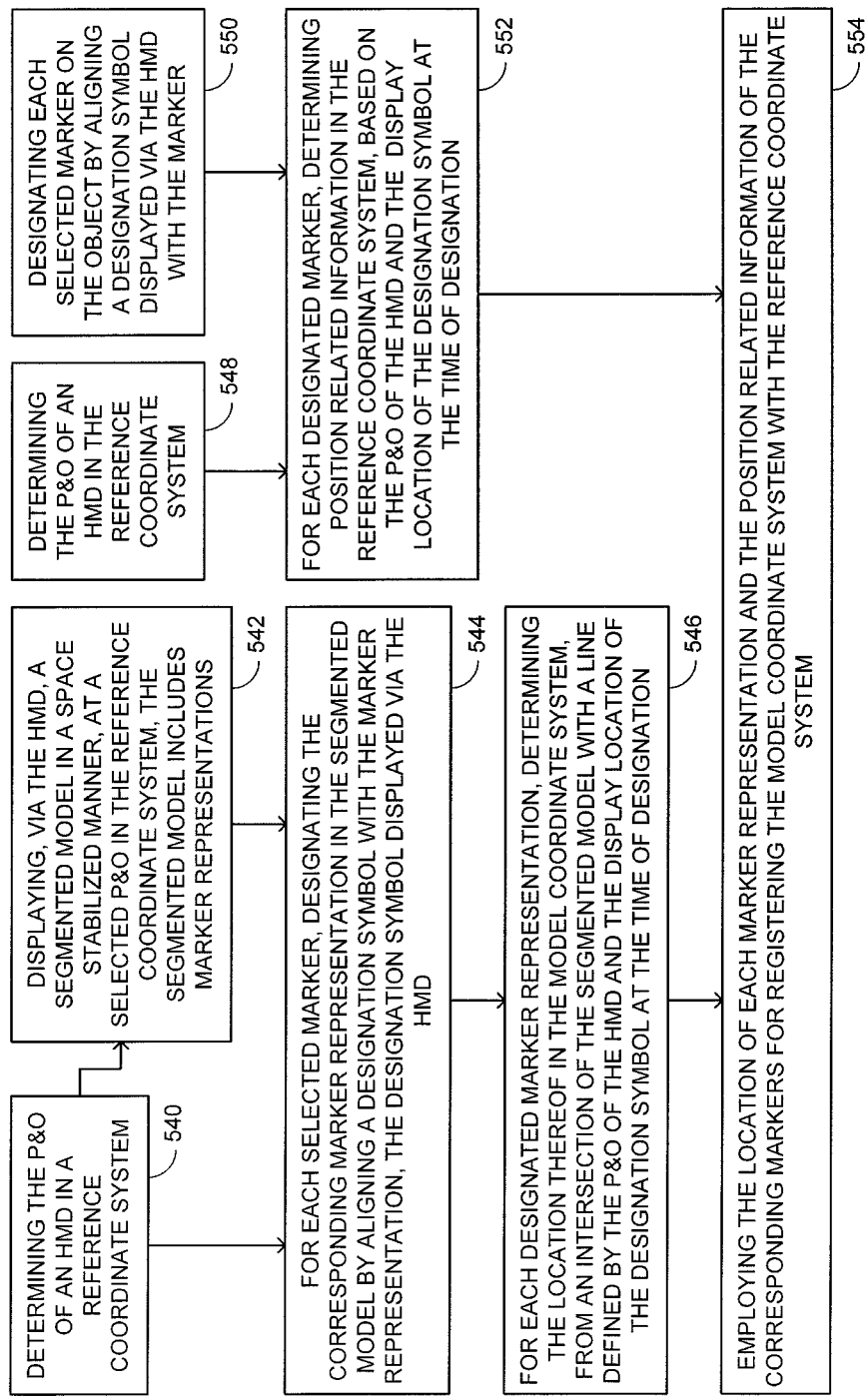
FIG. 11, which is a schematic illustration of a method for registering a model coordinate system and a reference coordinate system employing marker designation, in accordance with a further embodiment.

Reference is now made to FIG. 11, which is a schematic illustration of a method for registering a model coordinate system and a reference coordinate system employing marker designation, in accordance with a further embodiment. In procedure 540 the P&O of an HMD is determined in a reference coordinate system. With reference to FIG. 2 processor 214 determines the P&O of HMD 218 in reference coordinate system 230. From procedure 540, the method proceeds to procedures 542 and 544.

In procedure 542, a segmented model is displayed via the HMD, in a space stabilized manner, at a selected P&O in the reference coordinate system. The segmented model includes marker representations. With reference to FIGS. 2 and 8A processor 214 displays a segmented model 470 via visor 220, in a space stabilized manner at a selected P&O in the reference coordinate system 230.

In procedure 544, or each selected marker, the corresponding marker representation is designated in the segmented model by aligning a designation symbol with the marker representation, the designation symbol displayed via the HMD. The designation symbol is aligned with a respective location of each selected marker. With reference to FIGS. 8A-8G, each one of marker representations $472_1$-$472_6$ is designated by aligning designation symbol 476 with marker representations $472_1$-$472_6$.

In procedure 546, for each designated marker representation, the location thereof is determined in the model coordinate system, from an intersection of the segmented model with a line defined by the P&O of the HMD, and the display location of the designation symbol at the time of designation. With reference to FIG. 2, processor 214 determines the location of each designated marker representation from an intersection of the segmented model with a line defined by the P&O of the HMD and the display location of the designation symbol at the time of designation. From procedure 546 the method proceeds to procedure 554.

In procedure 548 the P&O of an HMD is determined in a reference coordinate system. With reference to FIG. 2 processor 214 determines the P&O of HMD 218 in reference coordinate system 230.

In procedure 550, each selected marker on the object is designated by aligning a designation symbol displayed via the HMD with the maker. With reference to FIGS. 2 and 7A-7I, designation symbol 466 is aligned with each of markers $460_1$-$460_6$.

In procedure 552, position related information is determined for each designated marker in the reference coordinate system, based on the P&O of the HMD and the display location of the designation symbol at the time of designation. As mentioned above, position related information at least includes a line in the reference coordinate system on which the marker is located. With reference to FIG. 2, processor 214 determines position related information for each designated marker. It is noted that procedures 548 and 550 may be performed before, after or in conjunction with procedures 540-546, as explained above.

In procedure 554, the model coordinate system is registered with the reference coordinate system employing the location of each marker representation and the position related information of the corresponding marker. With reference to FIG. 2, processor 214 registers the model coordinate system with the reference coordinate system employing the location of each marker representation and the position related information of the corresponding marker.

According to another example of registering a model with a reference coordinate system, the user translates, rotates and scales the model presented on the display until model is aligned with the object. The registration is determined from translation rotation and scale resulting in the alignment.

Figure 12C:
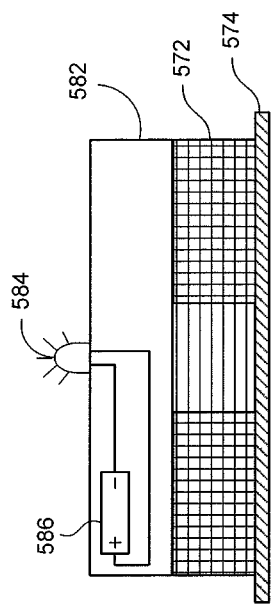
FIGS. 12C-12E are schematic illustrations of an exemplary active registration marker, constructed and operative in accordance with another embodiment.
Figure 12E:
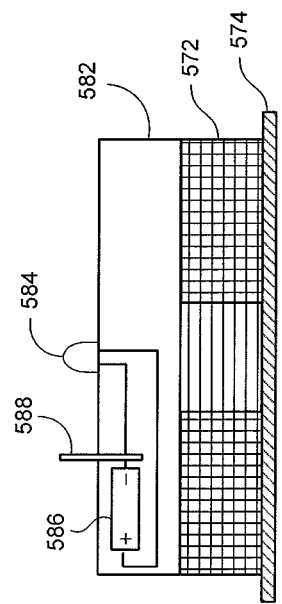
Figure 12D:
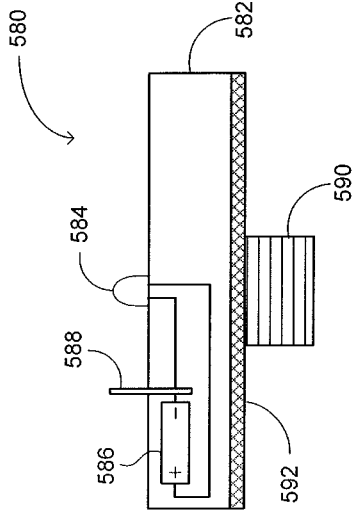

Reference is now made to FIGS. 12A-12E. FIGS. 12A and 12B are schematic illustrations of an exemplary standard marker, generally referenced 590. A standard marker 590 is employed during model acquisition (e.g., during CT or MRI imaging). FIGS. 12C-12E are schematic illustrations of an exemplary active registration marker, generally reference 580, constructed and operative in accordance with another embodiment, which may be attached to a standard marker 590. Active registration marker 580 is employed during registration. FIG. 12A is a top view of a standard marker 590 and FIG. 12B is a cross section view of a standard marker 590. In the example brought forth herein, the standard marker 590 is in the form of a ring which forms a cavity 598. Standard marker 590 includes a marker body 592, and a bottom sticker 594. Bottom sticker 594 is employed for attaching marker 590 to the patient. Marker body 592 is made of a material which may be detected in the acquired model (e.g., a radio-opaque material for CT imaging). Marker 590 may also have a cover 506 that protects the marker from damage and is removed before the registration process.

As mentioned above, the markers described hereinabove in conjunction with FIGS. 1A-1C 2, 3, 4, 5 and 6A-6D, 7A-7E and 8A-8H may be passive markers or active markers. A passive marker reflects the light impinging thereon. An active marker includes a LED and a battery and is activated just before initiation of the registration process starts. With reference to FIG. 12C, active registration marker 580 includes a housing 582, an LED 584, a power supply 586, a detachable isolator 588, a protrusion 590 and a sticker 592. LED 584 is coupled with power supply 586. Detachable isolator 588 isolates LED 584 from power supply 586. In general, power supply 586 takes the form of a battery. However, power supply 586 may also take to form of a preloaded capacitor. With reference to FIG. 12D, before active registration marker 580 is attached to standard marker 590, sticker 592 is removed exposing an adhesive. Thereafter, protrusion 590 is inserted into cavity 598 and housing 582 is fixedly attached to marker body 592. With reference to FIG. 12E, once active registration marker 580 is attached to marker body 592, detachable isolator 588 is removed thereby connecting LED 584 to power supply 586. Thus, LED 584 starts to emit light. When employing active registration markers such as LED, a suitable segmentation technique of an image of such active markers is Binary Large Object (BLOB) detection. The characteristics of the BLOBs corresponding to the active markers are employed for registration. For example the location of the BLOB in the image corresponds to a direction of the marker relative to the imager.

Figure 13:
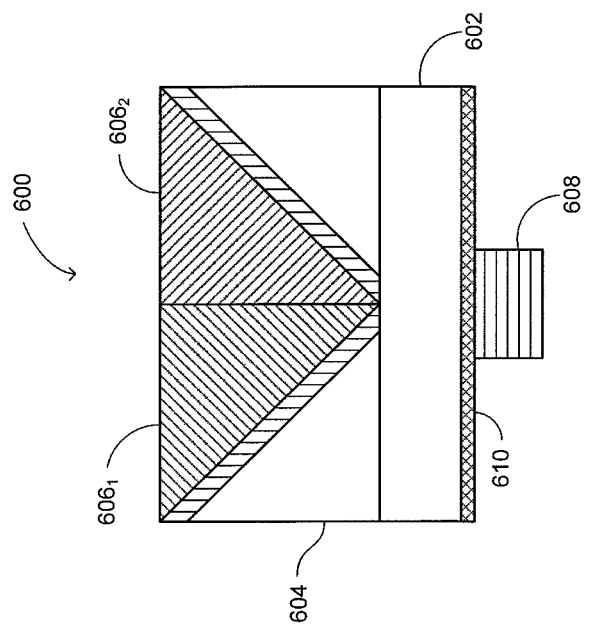
FIG. 13 is a schematic illustration of cross-sectional view of a passive registration marker, constructed and operative in accordance with a further embodiment.

As mentioned above, the registration marker may also be a passive registration marker. Such a passive registration marker may be a reflector or a retro-reflector. Reference is now made to FIG. 13, which is a schematic illustration of cross-sectional view of a passive registration marker, generally referenced 600, constructed and operative in accordance with a further embodiment. Passive registration marker 600 is exemplified herein as a corner cube retro-reflector. Passive registration marker includes a housing 602, a corner cube retro-reflector 604, a protrusion 608 and a sticker 610. Corner cube retro-reflector 604 includes three mirrors. Two mirrors 606$_1$ and 606$_2$, of the three mirrors included in a corner cube reflector 604 are depicted in FIG. 10. Light impinging on corner cube retro-reflector is reflected back toward the direction from which that light arrived. Similar to active registration marker 560 (FIGS. 12C-12E), passive registration marker may be fixedly attached to a standard marker such as marker 550 (FIGS. 12A-12B), after the model acquisition process and before the registration process.

In general, the passive registration marker 600 is illuminated with the LED located on the portable unit (e.g., LEDS 104$_1$ and 104$_2$ of FIG. 1 or LEDs 206$_1$ and 206$_2$ of FIG. 2). The optical detector located on the portable unit (e.g., optical detector 102 of FIG. 1 or optical detector 202 of FIG. 2) acquires an image of the light reflected from passive registration marker 600. Thus, when passive registration marker 600 is embodied as a retro-reflector, it is important that the light emitters of the portable unit be located sufficiently close to the optical detector such that the light that is retro-reflected from passive registration 600 could be detected by the optical detector.

Figure 14B:
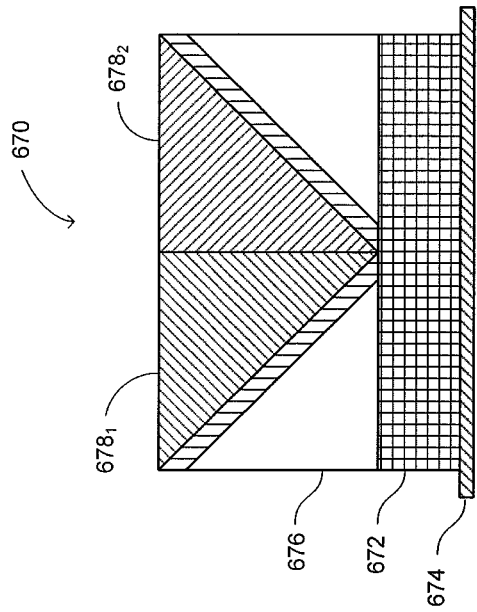
FIGS. 14A and 14B are schematic illustrations of two exemplary fiducial markers, which may be employed for both model acquisition and registration in accordance with another embodiment.
Figure 14A:
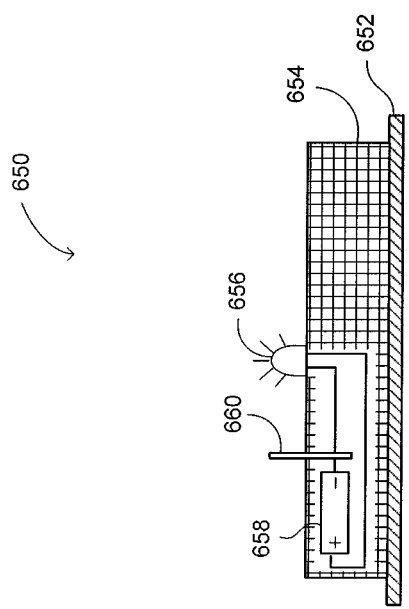

It is noted that, according to some embodiments, a single fiducial marker may be employed during both model acquisition and registration. Reference is now made to FIGS. 14A and 14B, which are schematic illustrations of two exemplary fiducial markers, generally reference 650 and 670 respectively, which may be employed for both model acquisition and registration in accordance with another embodiment. Fiducial marker 650 is an active fiducial marker and fiducial marker 670 is a passive fiducial marker.

With reference to FIG. 14A, fiducial marker 650 includes a body 652 which is made of a material which may be detected in the acquired model (e.g., a radio-opaque material for CT imaging), a sticker 654, a LED 656 a power supply 658 (e.g., a battery or a capacitor) and a detachable isolator 660. LED 656 is coupled with power supply 658. Detachable isolator 660 isolates LED 656 from power supply 658. Bottom sticker 654 is employed for attaching marker 650 to the patient. Thereafter, the model of the patient is acquired. Prior to the registration process, detachable isolator 660 is removed thereby connecting LED 606 to power supply 658. Thus, LED 606 starts to emit light.

With reference to FIG. 14B, fiducial marker 670 includes a body 672 is made of a material which may be detected in the acquired model, a sticker 674 and corner cube retro-reflector 676. Corner cube retro-reflector 676 includes three mirrors. Two mirrors 678$_1$ and 678$_2$, of the three mirrors included in a corner cube reflector 676 are depicted in FIG. 14B. Bottom sticker 674 is employed for attaching marker 670 to the patient. Thereafter, the model of the patient is acquired.

Similar to as describe above in conjunction with FIGS. 12A-12D and 13, a visual identifier can be attached to a standard fiducial at a defined location and employed during registration (e.g., an ArUco marker). Such a marker is referred to herein as an 'add-on marker'. The position of the visual identifier, relative to the location associated with the standard marker (e.g. the intersection of the axis of a ring-shaped fiducial with the skin, as determined in the 3D dataset), is known and used as describe hereinabove. The visual identifiers can be the same for all markers or each visual identifier can be unique. When the visual identifiers are unique (e.g., each visual identifier is a different ArUco marker), the visual identifies can be readily identified in various acquired images, allowing their respective locations (and orientations) to be averaged over multiple images.

According to another alternative, the marker can be manufactured such that at least part of the marker is visible in an acquired 3D dataset and the marker also includes a visual identifier. Such a marker is referred to herein as a 'manufactured dual marker'. The relative position between the part of the marker that can be visible in the 3D dataset and the visual identifier is known and used by the processor during the registration. The part of the marker that can be visible in the acquired dataset can be unique (e.g., a plurality of small radio-opaque balls for CT imaging, in a unique spatial arrangement). The visual identifier can also be unique.

Both the add-on marker and the manufactured dual-marker can be provided as sets or kits. For example, a kit can comprise 10 unique add-on markers or 10 unique manufactured dual markers. For example, the user can open a kit of add-on markers and attach them to the standard fiducials. In another example, a radiology technician can open a kit of manufactured dual markers and adhere them to the patient.

It will be appreciated by persons skilled in the art that the disclosed embodiments are not limited to what has been particularly shown and described hereinabove. Rather the scope of the disclosed embodiments is defined only by the claims, which follow.

The invention claimed is:

1. A system for registering a coordinate system associated with a model of an object with a reference coordinate system, said object including at least one marker, the system comprising:
    a portable unit including:
        a display; and
        an optical detection assembly configured to acquire at least one representation of said at least one marker;
    a tracking system configured to track the position and orientation of said portable unit in said reference coordinate system; and
    a processor, coupled with said portable unit and with said tracking system,
    said processor configured to determine position related information respective of said at least one marker in said reference coordinate system, from said at least one representation and said position and orientation of said portable unit,
    said processor further configured to register said model with said reference coordinate system at least based on said position related information respective of said at least one marker in said reference coordinate system, and based on a location of said at least one marker in said coordinate system associated with said model,
    said processor further configured to display registration related information on said display, at least one of said registration related information or display location of said registration related information being related to the position and orientation of said portable unit in said reference coordinate system.

2. The system according to claim 1, wherein said model is a three dimensional dataset of a region of interest of said object.

3. The system according to claim 1, wherein said registration is for a medical procedure and said model is acquired either pre-operatively or intra-operatively.

4. The system according to claim 1, wherein said registration is for a medical procedure and said marker is at least one of:
    an artificial marker;
    an anatomical landmark; or
    an anatomical surface.

5. The system according to claim 1, wherein said portable unit is at least one of:
    a head mounted unit;
    a unit attached to a movable arm; or
    a hand held unit.

6. The system according to claim 1, wherein said optical detection assembly is one of:
    a camera;
    a stereoscopic camera;
    a laser scanner;
    a structured light scanner;
    a time-of-flight camera; or
    a Position Sensitive Device.

7. The system according to claim 1, wherein said at least one representation of said at least one marker is one of:
    at least one image of said at least one marker;
    a surface scan of said at least one marker; or
    a signal indicative of a direction toward said at least one marker.

8. The system according to claim 1, wherein said position related information respective of said at least one marker includes at least one of:
    a location respective of said at least one marker in said reference coordinate system;
    at least one vector in said reference coordinate system pointing toward a location respective of said at least one marker; or
    a surface defined in the reference coordinate system.

9. The system according to claim 8, wherein said processor is configured to determine said location respective of said marker in said reference coordinate system based on at least one of:
    at least two vectors; or
    a vector and a distance.

10. The system according to claim 1, wherein said processor is configured to determine said position related information further based on:
    a location respective of said at least one marker in said at least one representation, said at least one representation acquired by a sensor in said optical detection assembly;
    a predetermined calibration of said sensor; and
    an alignment between a coordinate system of said sensor and a coordinate system of said portable unit.

11. The system according to claim 1, wherein said at least one representation is an image, and said processor is further configured to determine a location of said at least one marker in said image, and said position related information is based on said location.

12. The system according to claim 11, wherein a user designates at least one area on said object and said processor is configured to determine a location of said at least one marker representation in a region of interest corresponding to said area in said image.

13. The system according to claim 1, wherein said registration related information includes at least one of:
    a marker indicator;
    a marker identifier;
    an error associated with the determined location of a marker;
    a registration score;
    instructions to said user;
    user selection options; or
    a segmented model.

14. A method for registering a coordinate system associated with a model of an object with a reference coordinate system, said object including at least one marker, the method including:
    acquiring at least one representation of said at least one marker;
    tracking the position and orientation of a portable unit in said reference coordinate system;
    determining position related information respective of said at least one marker in said reference coordinate system, from said at least one representation and said position and orientation of said portable unit;
    registering said model with said reference coordinate system at least based on said position related information respective of said at least one marker in said reference coordinate system, and based on a location of said at least one marker in said coordinate system associated with said model; and
    displaying registration related information, at least one of said registration related information or a display location of said registration related information being related to the position and orientation of said portable unit in said reference coordinate system.

15. The method according to claim 14, wherein said model is a three dimensional dataset of a region of interest of said object.

16. The method according to claim 14, wherein said registration is for a medical procedure and said model is acquired either pre-operatively or intra-operatively.

17. The method according to claim 14, wherein said registration is for a medical procedure and said marker is at least one of:
   an artificial marker;
   an anatomical landmark; or
   and anatomical surface.

18. The method according to claim 14, wherein the portable unit includes an optical detection assembly configured to acquire said at least one representation of said at least one marker, wherein said optical detection assembly is one of:
   a camera;
   a stereoscopic camera;
   a laser scanner;
   a structured light scanner;
   a time-of-flight camera; or
   a Position Sensitive Device.

19. The method according to claim 14, wherein said at least one representation of said at least one marker is one of:
   at least one image of said at least one marker;
   a surface scan of said at least one marker; or
   a signal related to a direction toward said at least one marker.

20. The method according to claim 14, wherein said position related information respective of said at least one marker includes at least one of:
   a location respective of said at least one marker in said reference coordinate system;
   at least one vector in said reference coordinate system pointing toward a location respective of said at least one marker; or
   a surface defined in the reference coordinate system.

21. The method according to claim 20, wherein determining said position related information includes determining a location of said marker in said reference coordinate system based on at least one of:
   at least two vectors; or
   a vector and a distance.

22. The method according to claim 14, wherein the portable unit includes an optical detection assembly configured to acquire said at least one representation of said at least one marker, wherein said determining position related information is based on:
   a location respective of said at least one marker in said at least one representation, said at least one representation acquired by a sensor in said optical detection assembly;
   a predetermined calibration of said sensor; and
   an alignment between a coordinate system of said sensor and a coordinate system of said portable unit.

23. The method according to claim 14, wherein said at least one representation is an image, and determining said position related information includes determining a location of said at least one marker in said image, and said position related information is based on said location.

24. The method according to claim 23, wherein a user designates at least one area on said object and determining said position related information includes determining a location of said at least one marker representation in a region of interest corresponding to said area in said image.

25. The method according to claim 14, wherein said registration related information includes at least one of:
   a marker indicator;
   a marker identifier;
   an error associated with the determined location of a marker;
   a registration score;
   instructions to said user;
   user selection options; or
   a segmented model.

* * * * *